United States Patent
Wang et al.

(10) Patent No.: US 6,288,297 B1
(45) Date of Patent: Sep. 11, 2001

(54) PROCESS FOR THE PREPARATION OF CYCLOPROPYLACETYLENE

(75) Inventors: Zhe Wang, Hockessin; Jianguo Yin, Wilmington; Joseph M. Fortunak, Newark; Silvio Campagna, New Castle, all of DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/410,481

(22) Filed: Sep. 30, 1999

Related U.S. Application Data

(60) Provisional application No. 60/102,644, filed on Oct. 1, 1998.

(51) Int. Cl.⁷ .................................................. C07C 1/207
(52) U.S. Cl. ........................ 585/538; 585/357; 585/359
(58) Field of Search ................................. 585/359, 357, 585/538

(56) References Cited

U.S. PATENT DOCUMENTS

| | | | |
|---|---|---|---|
| 5,250,540 | 10/1993 | Arlt et al. | 514/302 |
| 5,318,988 | 6/1994 | Schohe-Loop et al. | 514/458 |
| 5,407,599 | 4/1995 | De Maijere et al. | 252/299 |
| 5,468,882 | 11/1995 | Schohe-Loop et al. | 549/407 |
| 5,519,021 | 5/1996 | Young et al. | 514/230 |
| 5,663,467 | 9/1997 | Thompson et al. | 585/359 |
| 5,952,537 | * 9/1999 | Stickley et al. | |
| 5,955,627 | * 9/1999 | Nakazawa et al. | |
| 6,028,237 | * 2/2000 | Parsons, Jr. | |
| 6,049,019 | * 4/2000 | Fortunak et al. | |
| 6,072,094 | * 6/2000 | Karady et al. | |

FOREIGN PATENT DOCUMENTS

| | | |
|---|---|---|
| 0847974 | 6/1998 | (EP) . |
| 9622955 | 8/1996 | (WO) . |
| 9637457 | 11/1996 | (WO) . |

OTHER PUBLICATIONS

Craig et al., Angew. Chem. Int. Ed. Engl., (1969), 8(6), 429–437.
Schoberth and Hanack, Synthesis (1972), (12), 703.
Taguchi et al., J. Am. Chem. Soc., (1974), 96(9), 3010–3011.
Wong and Ho, Synthetic Communications, (1974), 4(1), 25–27.
Villieras et al., Synthesis, (1975), 458–461.
Tsuji et al., Chemistry Letters, (1979), 481–482.
Van Hijfte et al., Tetrahedron Letters, (1989), 30(28) 3655–3656.
Corey et al., Tetrahedron Letters, (1992), 33(24), 3435–3438.
Grandjean et al., Tetrahedron Letters, (1994), 35(21), 3529–3530.
Thompson et al., Tetrahedron Letters, (1995), 36(49), 8937–8940.
Ihara et al., Tetrahedron, (1995), 51(36), 9873–9890.
Bunnage and Nicolaou, Angew. Chem. Int. Ed. Engl., (1996), 35(10), 1110–1112.
Carl Bernard Ziegler, Jr., Syhthesis and Mechanistic Studies of Polyunsaturated Fatty Acid Hydroperoxides Involving a Novel Vinylcyclopropyl Bromide Ring., Ph.D. Dissertation, Duke University (1981), 139 pp.

* cited by examiner

*Primary Examiner*—Jerry D. Johnson

(57) ABSTRACT

The present invention relates generally to novel methods for the synthesis of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor. In the process, for example, cyclopropane carboxaldehyde is alkylated to form 1,1,1-trichloro-2-cyclopropyl-ethanol; which in turn is hydroxy protected to form 1,1,1-trichloro-2-cyclopropylethyltosylate; which in turn undergoes elimination to form cyclopropyl acetylene. This improvement provides for high conversion of inexpensive, readily available starting materials into cyclopropylacetylene, high overall yields and can be conducted on an industrial scale.

19 Claims, No Drawings

PROCESS FOR THE PREPARATION OF CYCLOPROPYLACETYLENE

This application claims benefit of Provisional Application Ser. No. 60/102,644 filed Oct. 1, 1998.

FIELD OF THE INVENTION

The present invention relates generally to novel methods for the synthesis of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor. In the process, for example, cyclopropane carboxaldehyde is alkylated to form 1,1,1-trichloro-2-cyclopropyl-ethanol; which in turn is hydroxy protected to form 1,1,1-trichloro-2-cyclopropylthyltosylate; which in turn undergoes elimination to form cyclopropyl acetylene.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (VI):

(VI)

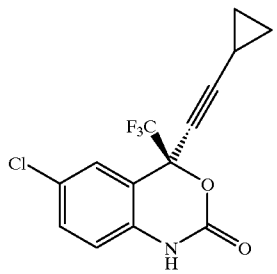

is not only a highly potent reverse transcriptase inhibitor, it is also efficacious against HIV reverse transcriptase resistance. Due to the importance of (S)-6-chloro-4-cyclopropylethynyl-4-trifluoromethyl-1,4-dihydro-2H-3,1-benzoxazin-2-one as a reverse transcriptase inhibitor, economical and efficient synthetic processes for its production need to be developed.

Cyclopropylacetylene is an important reagent in the synthesis of compound (VI). Thompson et al, *Tetrahedron Letters* 1995, 36, 937–940, describe the asymmetric synthesis of an enantiomeric benzoxazinone by a highly enantioselective acetylide addition followed by cyclization with a condensing agent to form the benzoxazinone shown below. As a reagent the cyclopropylacetylene was synthesized in a 65% yield by cyclization of 5-chloropentyne with n-butyllithiun at 0°–80° C. in cyclohexane followed by quenching with ammonium chloride. The process generates a low yield of cyclopropylacetylene which is not feasible for the large commercial process of a difficult to handle reagent.

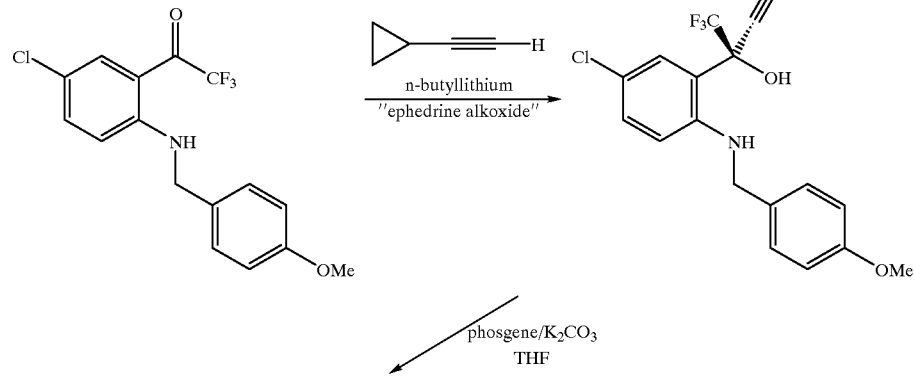

-continued

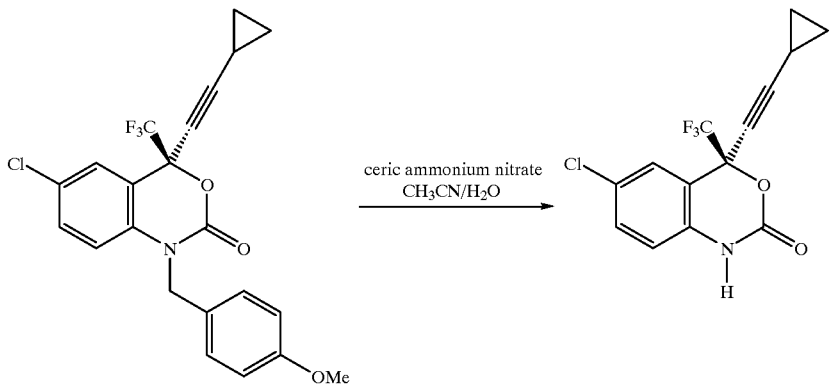

Thompson et al, PCT International Patent Application Number WO 9622955 A1 describe an improved synthesis of cyclopropylacetylene useful in the synthesis of (S)-6-chloro-4-cyclopropylethynyl-4-trifluoromethyl-1,4-dihydro-2H-3,1-benzoxazin-2-one. Application WO 9622955 A1 discloses methods which continue to be inefficient in the overall synthesis on a kilogram scale for which this invention makes significant improvements.

The chemical literature shows the majority of the cyclopropylacetylene preparations involve the conversion of cyclopropylmethyl ketone to cyclopropyl-acetylene via the following chemical scheme. The method will produce cyclopropylacetylene on small scale, <1 kilogram, but is not amenable for bulk production, thus an alternative was developed.

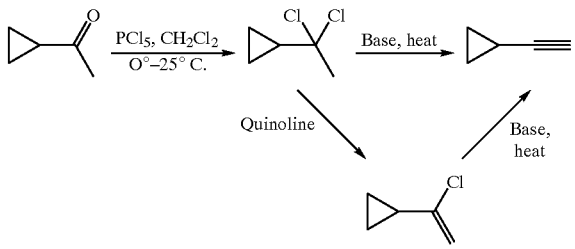

The above methods for the synthesis of cyclopropylacetylene use combinations of toxic, difficult to handle reagents, relatively expensive materials, incomplete conversions and low yields which render the overall synthesis inefficient and yield cyclopropylacetylene of lower purity. Thus, it is desirable to discover new synthetic routes to cyclopropylacetylene on a large scale which improve upon these limitations and provide high yields of desired cyclopropylacetylene.

The present invention discloses a novel scalable procedure for the preparation of substituted acetylenes, more specifically cyclopropylacetylene. Improvements over previously disclosed preparations of cyclopropyl acetylene are in the low economic price and availability of the starting materials; the convenience and high yields for the chemistry; and the ability to crystallize and store without degradation the intermediates. The invention provides novel chemistry for the production of cyclopropyl acetylene from cyclopropane carboxaldehyde. The process provides a high yield (>90%) for the convenient reaction of cyclopropane carboxaldehyde with trichloroacetic acid to give 1,1,1-trichloro-2-cyclopropylethanol. The subsequent transformation of 1,1,1-trichloro-2-cyclopropylethanol to 1,1,1-trichloro-2-cyclopropyl-2-ethanyltosylate occurs in high yield using convenient reaction conditions. The final preparation of cyclopropylacetylene by dehalogenation from 1,1,1-trichloro-2-cyclopropyl-2-ethanyltosylate proceeds in high yields and with suitable purities so that the cyclopropyl acetylene produced and isolated can be stored or used as a solution in an inert solvent.

None of the above-cited references describe the methods of the present invention for the synthesis of substituted acetylenes, in particular, cyclopropylacetylene.

SUMMARY OF THE INVENTION

The present invention concerns an improved process suitable for the large scale preparation of cyclopropylacetylene. In the process, cyclopropane carboxaldehyde is condensed with an alkylating/halogenating agent, such as trichloroacetic acid, to form 1,1,1-trichloro-2-cyclopropylethanol; 1,1,1-trichloro-2-cyclopropylethanol is protected to form 1,1,1-trichloro-2-cyclopropyl-2-ethanyltosylate; and 1,1,1-trichloro-2-cyclopropyl-2-ethanyltosylate is dehalogenated to form cyclopropyl acetylene. This improvement provides for high conversion of inexpensive, readily available starting materials into cyclopropyl acetylene, high overall yields and can be conducted on an industrial scale.

DETAILED DESCRIPTION OF THE INVENTION

In a first embodiment, the present invention provides a process for the preparation of compound of formula (IV);

(IV)

wherein:
$R^1$ is selected from:
  $C_{1-10}$ alkyl substituted with 0–3 $R^4$,
  $C_{2-6}$ alkenyl substituted with 0–1 $R^4$,
  $C_{3-10}$ cycloalkyl substituted with 0–2 $R^5$,
  $C_{3-6}$ carbocyclic ring substituted with 0–2 $R^5$, and
  aryl substituted with 0–2 $R^6$;
$R^4$, at each occurrence, is selected from $OR^7$, $NR^7R^{7a}$, phenyl, and cyclopropyl;
$R^5$, at each occurrence, is selected from D, methyl, ethyl, propyl, methoxy, ethoxy, and propoxy;
$R^6$, at each occurrence, is selected from methyl, ethyl, propyl, methoxy, ethoxy, propoxy, F, Cl, B, I, CN, and $NR^7R^{7a}$;

$R^7$ and $R^{7a}$ are independently selected from methyl, ethyl, propyl, and butyl;

said process comprising:

(1) contacting an aldehyde of formula $R^1$—CHO with trichloroacetic acid or tribromoacetic acid, in the presence of a base catalyst to form a compound of formula (II):

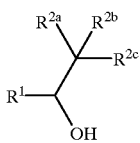
(II)

wherein $R^{2a}$, $R^{2b}$, and $R^{2c}$ are Cl or Br;

(2) contacting a compound of formula (II) with a hydroxy group protecting agent in the presence of a coupling catalyst and an acid scavenger, in a suitable nonaqueous solvent to form a compound of formula (III)

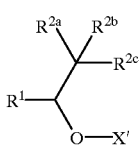
(III)

wherein —X' is a hydroxy protecting group; and (3) contacting a compound of formula (III) with a strong base to form a compound of formula (IV).

In a preferred embodiment, the present invention provides a process for the preparation of cyclopropylacetylene, said process comprising:

(1) contacting cyclopropane carboxaldehyde with trichloroacetic acid or tribromoacetic acid, in the presence of a base catalyst to form a compound of formula (IIa)

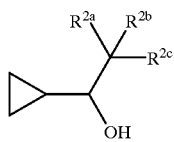
(IIa)

wherein $R^{2a}$, $R^{2b}$, and $R^{2c}$ are Cl or Br;

(2) contacting a compound of formula (IIa) with a sulfonyl hydroxy group protecting agent in the presence of a coupling catalyst and an acid scavenger, in a suitable nonaqueous solvent to form a compound of formula (IIIa)

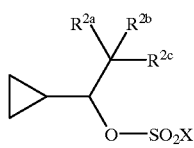
(IIIa)

wherein —SO$_2$X is a sulfonyl hydroxy protecting group; and (3) contacting a compound of formula (IIIa) with a strong base to form cyclopropyl acetylene.

In a further preferred embodiment cyclopropane carboxaldehyde is contacted with trichloroacetic acid in the presence of a base catalyst to form a compound of formula (II) wherein $R^{2a}$, $R^{2b}$, and $R^{2c}$ are Cl.

In a further preferred embodiment the sulfonyl hydroxy group protecting agent comprises toluenesulfonyl chloride or methanesulfonyl chloride.

In a further preferred embodiment the base catalyst comprises sodium trichloroacetate.

In a further preferred embodiment the coupling catalyst comprises 1,4-diazabicyclo[2.2.2]octane.

In a further preferred embodiment the acid scavenger comprises triethylamine.

In a further preferred embodiment the strong base comprises sodium amide or methyl lithium.

In an even more preferred embodiment, the present invention provides a process for the preparation of cyclopropylacetylene comprising:

(1) contacting cyclopropane carboxaldehyde with trichloroacetic acid in the presence of trichloroacetic acid to form a compound of formula (IIa)

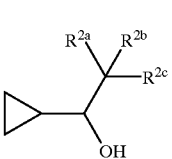
(IIa)

wherein $R^{2a}$, $R^{2b}$, and $R^{2c}$ is Cl;

(2) contacting a compound of formula (IIa) with a toluenesulfonyl chloride or methanesulfonyl chloride in the presence of 1,4-diazabicyclo[2.2.2]octane and triethylamine, in a suitable nonaqueous solvent to form a compound of formula (IIIa)

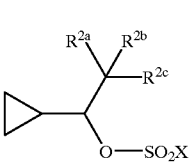
(IIIa)

wherein —SO$_2$X is toluenesulfonyl or methanesulfonyl; and (3) contacting a compound of formula (IIIa) with a methyl lithium or sodium amide to form cyclopropyl acetylene.

In a second embodiment, the present invention provides a process for synthesis of a compound of formula (IV);

(IV)

wherein;

$R^1$ is selected from:
- C$_{1-10}$ alkyl substituted with 0–3 $R^4$,
- C$_{2-6}$ alkenyl substituted with 0–1 $R^4$,
- C$_{3-10}$ cycloalkyl substituted with 0–2 $R^5$,
- C$_{3-6}$ carbocyclic ring substituted with 0–2 $R^5$, and
- aryl substituted with 0–2 $R^6$;

$R^4$, at each occurrence, is selected from OR$^7$, NR$^7$R$^{7a}$, phenyl, and cyclopropyl;

$R^5$, at each occurrence, is selected from D, methyl, ethyl, propyl, methoxy, ethoxy, and propoxy;

$R^6$, at each occurrence, is selected from methyl, ethyl, propyl, methoxy, ethoxy, propoxy, F, Cl, B, I, CN, and $NR^7R^{7a}$;

$R^7$ and $R^{7a}$ are independently selected from methyl, ethyl, propyl, and butyl;

said process comprising:

(1) contacting an aldehyde of formula $R^1$—CHO with dichloromethane or dibromomethane, in the presence of a base catalyst to form a compound of formula (II):

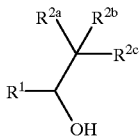

(II)

wherein: $R^{2a}$ is H and $R^{2b}$ and $R^{2c}$ are Cl or Br;

(2) contacting a compound of formula (II) with a hydroxy group protecting agent in the presence of an acid scavenger, in a suitable nonaqueous solvent to form a compound of formula (III)

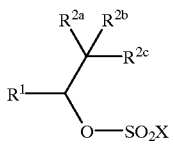

(III)

wherein —$SO_2X$ is a hydroxy protecting group; and (3) contacting a compound of formula (III) with a strong base to form a compound of formula (IV).

In a preferred embodiment, the present invention provides a process for the preparation of cyclopropylacetylene, said process comprising:

(1) contacting cyclopropane carboxaldehyde with dichloromethane or dibromomethane, in the presence of a base catalyst to form a compound of formula (IIaa)

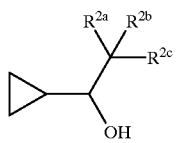

(IIaa)

wherein: $R^{2a}$ is H and $R^{2b}$ and $R^{2c}$ are Cl or Br;

(2) contacting a compound of formula (IIaa) with a sulfonyl hydroxy group protecting agent in the presence of a coupling catalyst and an acid scavenger, in a suitable nonaqueous solvent to form a compound of formula (IIIaa)

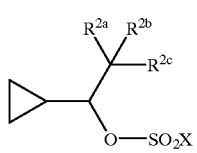

(IIIaa)

wherein —$SO_2X$ is a sulfonyl hydroxy protecting group; and (3) contacting a compound of formula (IIIaa) with a strong base to form cyclopropyl acetylene.

In a further preferred embodiment cyclopropane carboxaldehyde is contacted with dichloromethane in the presence of a base catalyst to form a compound of formula (IIaa) wherein $R^{2a}$ is H and $R^{2b}$ and $R^{2c}$ are Cl.

In a further preferred embodiment the sulfonyl hydroxy group protecting agent comprises toluenesulfonyl chloride or methanesulfonyl chloride.

In a further preferred embodiment the base catalyst comprises sodium trichloroacetate.

In a further preferred embodiment the acid scavenger comprises triethylamine.

In a further preferred embodiment the strong base comprises sodium amide or methyl lithium.

The processes of the present invention are useful for the preparation of cyclopropylacetylene, an essential intermediate in the synthesis of (S)-6-chloro-4-cyclopropylethynyl-4-trifluoromethyl-1,4-dihydro-2H-3,1-benzoxazin-2-one, which is useful as a human immunodeficiency virus (HIV) reverse transcriptase inhibitor, and compounds which are useful intermediates in the synthesis of (S)-6-chloro-4-cyclopropylethynyl-4-trifluoromethyl-1,4-dihydro-2H-3,1-benzoxazin-2-one. Such HIV reverse transcriptase inhibitors are useful for the inhibition of HIV and the treatment of HIV infection. Such HIV reverse transcriptase inhibitors are useful for the inhibition of HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standards or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature, unless the purpose of the solvent is to quench the reaction. A given reaction may be carried out in one solvent or a mixture of more than one solvent. Depending on the particular reaction step, suitable solvents for a particular reaction step may be selected independent of any other reaction step.

Suitable halogenated solvents include chlorobenzene, dichloromethane, chloroform, carbon tetrachloride, dichlorobenzene, dichloroethane, and trichloroethane.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, anisole, or t-butylmethyl ether.

Suitable hydrocarbon or aromatic solvents include: benzene, cyclohexane, pentane, hexane, toluene, cycloheptane, methylcyclohexane, heptane, ethylbenzene, m-xylene, o-xylene, p-xylene, octane, indane, nonane, naphthalene and mesitylene(s).

As used herein, the term "base catalyst" refers to any agent which catalyzes the alkylation of cyclopropyl carboxaldehyde by the anion of trihalomethane or dihalomethane thus effecting the formation of a halogenated cyclopropyl carbinol. Examples of base catalysts, depending on the source of anion, include, but are not limited to, sodium trihaloacetate, sodium acetate, sodium hydride, sodium hydroxide, sodium methoxide, sodium ethoxide, potassium t-butoxide, lithium amide, lithium dialkyl amides, lithium diisopropyl amide (LDA), KHMDA, and LiHMDA.

As used herein, the term "acid scavenger" refers to any base the presence of which in the reaction facilitates the neutralization of HCl or HBr produced. Suitable acid scavengers may be selected by one of skill in the art of organic synthesis. Suitable acid scavengers include, but are not limited to, inorganic bases such as alkali metal, alkali earth metal, and ammonium hydroxides and alkoxides. Suitable acid scavengers also include, but are not limited to, metal amides and alkyl lithiums. Examples of suitable acid scavengers are lithium diisopropyl amide, sodium amide, sodium methoxide, potassium t-butoxide, sodium butoxide, potassium and sodium t-amyloxide, potassium hydroxide, sodium hydroxide, methyllithium, butyllithium, hexyllithium, phenyllithium, and tertiary alkylammonium hydroxides.

As used herein, the term "coupling agent" refers to any base the presence of which in the reaction facilitates the deprotonation of the carbinol OH proton and promotes protection of the alcohol by an alcohol protecting group. Suitable coupling agents may be selected by one of skill in the art of organic synthesis. Suitable coupling agents include, but are not limited to, pyridine, pyrrolidine, piperidine, morpholine, N-methylmorpholine, 1,4-diazabicyclo[2.2.2]octane (DABCO™), N,N-diethylaniline, N,N-dimethylaminopyridine(s), quinoline, and N,N-diisopropylethylamine; as well as sodium, potassium, lithium or cesium hydroxide; sodium, potassium, lithium or cesium carbonate; and alkoxide bases such as sodium, lithium or potassium methoxides, ethoxides, butoxides, t-butoxides, and t-amyloxides.

As used herein, the term "hydroxy group protecting agent" or "alcohol protecting agent" refers to any reagent suitable to convert a hydroxyl group to a leaving group, the presence of which in the reaction converts the OH of carbinol of formula 2 into a leaving group. A variety of such reagents will be appreciated by one of skill in the art of organic synthesis. Such reagents may be selected from, for example but not limited to, reagents of formula $ClSO_2X$ such as benzenesulfonyl chloride, toluenesulfonyl chloride, dimethylbenzenesulfonyl chloride, trimethylbenzene sulfonyl chloride, chlorobenzenesulfonyl chloride, dichlorobenzenesulfonyl chloride, trichlorobenzenesulfonyl chloride, methanesulfonyl chloride, ethanesulfonyl chloride, propanesulfonyl chloride, butanesulfonyl chloride. Such reagents may also be selected from, for example but not limited to, reagents of anhydrides, such as acetyl anhydride, tosyl anhydride, and mesylanhydride. Such reagents may also be selected from, for example but not limited to, reagents of acid chlorides, such as acetyl chloride.

As used herein, the term "sulfonyl hydroxy group protecting agent" is a subset of "hydroxy group protecting agent" which comprises substituted sulfonyl chlorides and substituted sulfonyl anhydrides.

As used herein, the term "hydroxy protecting group" or "OH protecting group" refers to any group derived from the "hydroxy group protecting agent" which replaces the proton of the OH of carbinol of formula 2 after reaction of the carbinol with a "hydroxy group protecting agent". A variety of such reagents will be appreciated by one of skill in the art of organic synthesis. Such reagents may be selected from, for example but not limited to, radicals of formula $-SO_2X$, such as benzenesulfonyl, toluenesulfonyl, dimethylbenzenesulfonyl, trimethylbenzene sulfonyl, chlorobenzenesulfonyl, dichlorobenzenesulfonyl, trichlorobenzenesulfonyl, methanesulfonyl, ethanesulfonyl, propanesulfonyl, butanesulfonyl. Such reagents may also be selected from, for example but not limited to, radicals derived from anhydrides, such as acetyl, tosyl, and mesyl. Such reagents may also be selected from, for example but not limited to, radicals derived from acid chlorides, such as acetyl.

As used herein, the term "sulfonyl hydroxy protecting group" is a subset of "hydroxy protecting group" which comprises substituted sulfonyls, for example $-SO_2X$.

As used herein, the term "strong base" refers to any organometallic base the presence of which in the reaction facilitates the synthesis of cyclopropyl acetylene from dihalo or trihalo compounds of formula 3. Suitable strong bases may be selected by one of skill in the art of organic synthesis. Suitable strong bases include, but are not limited to, metal amides, alkyl lithiums, and grignard reagents. Such strong bases include sodium amide, potassium amide, lithium amide, lithium diisopropylamide, methyllithium, butyllithium, hexyllithium, phenyllithium, and butyl magnesium chloride. Examples of suitable strong bases are sodium amide, sodium methoxide, potassium t-butoxide, sodium butoxide, potassium and sodium t-amyloxide, potassium hydroxide, sodium hydroxide, methyllithium, butyllithium, hexyllithium, phenyllithium.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Synthesis

It is the object of the present invention to provide a novel and improved process for the synthesis of substituted acetylenes, more specifically cyclopropylacetylene, which are useful in the synthesis of benzoxazinones which are useful as HIV reverse transcriptase inhibitors. The methods of the present invention, by way of example and without limitation, may be further understood by reference to Scheme 1. Scheme 1 details the improved general synthetic method for synthesis of $R^1$ substituted acetylenes by the present invention. In Scheme 1 $R^{2a}$ is H, Cl, or Br; $R^{2b}$ is Cl or Br; and $R^{2c}$ is Cl or Br. However, when $R^{2a}$ is H, then $R^{2b}$ and $R^{2c}$ are Cl or Br. Additionally, when $R^{2a}$ is Cl or Br, then $R^{2a}=R^{2b}=R^{2c}$.

Scheme 1

Step 1: Alkylation of Aldehyde

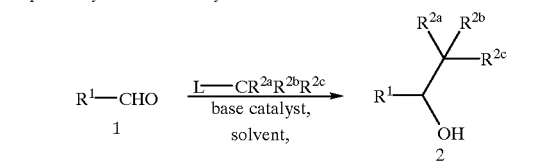

Step 2: Alcohol Protection

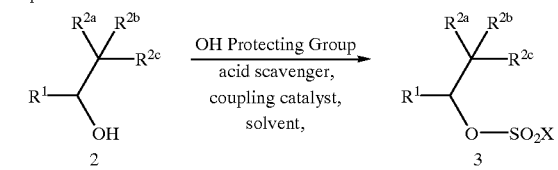

Step 3: Elimination

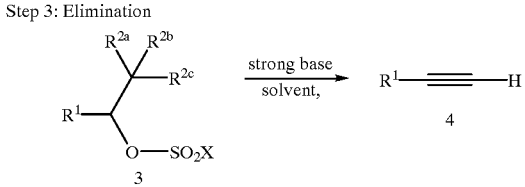

The methods of the present invention, by way of example and without limitation, may be further understood by reference to Scheme 2. Scheme 2 details the improved general synthetic method for synthesis of $R^1$ substituted acetylenes by the present invention wherein alkylation of cyclopropyl carboxaldehyde by a trihalo —$CR^{2a}R^{2b}R^{2c}$ anion is generated from trichloroacetic acid, or optionally tribromoacetic acid.

Scheme 2

Step 1:

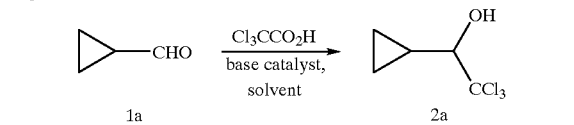

Step 2:

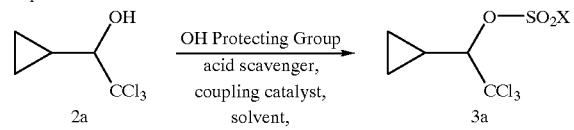

Step 3:

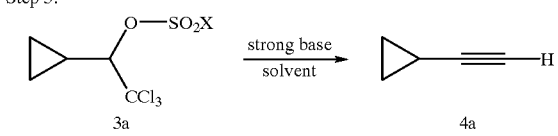

Step 1. Alkylation of Cyclopropylcarboxaldehyde

This step is conducted by reacting cyclopropyl carboxaldehyde in a suitable nonaqueous solvent at a suitable temperature with trichloroacetic acid in the presence of a suitable base catalyst to form cyclopropyltrichlorocarbinol of formula 2a. By way of general guidance, a reaction vessel is charged with a solution of trichloroacetic acid (about 1.2 to about 2.0 equivalents, preferably 1.5 eq) in a nonaqueous solvent. The aldehyde (about 1 eq.) is added into the solution preferably with a continues $N_2$ flow. To this stirred solution is added a base catalyst (about 1.2 to about 2.0 equivalents, preferably 1.5 eq) portionwise. The $N_2$ flow, if used, is stopped and the heterogeneous mixture is stirred at room temperature for preferably about 2 hours with continuous evolution of $CO_2$. Generally, the reaction can be monitored by $^1$H-NMR indicating the reaction completion by total disappearing of the aldehyde proton signal. The reaction mixture can be cooled to 5° C. and the product, 2a, isolated by work up. Examples of standard work up are shown in Examples 1 and 2. Isolation of the trichlorocarbinol is preferred but not necessary. The crude trichlorocarbinol is obtained in relative good purity and but can be purified by flash chromatography or distillation.

It is preferred that the reaction vessel is dried (for example by heat-air-gun or oven) and equipped with mechanical stirrer, nitrogen inlet and an outlet connected to a bubbler.

Suitable nonaqueous solvents are any amide solvents and sulfoxide solvents in which the aldehyde is soluble. These include, but are not limited to, dimethylformamide, dimethylsulfoxide, and 1-methyl-2-pyrrolidinone. Preferred nonaqueous solvent is dimethylformamide.

The concentration of aldehyde in the solvent may range from about 0.5 molar to about 3.0 molar. Preferred is 0.5 molar to 2.0 molar; more preferred is 1.0 molar.

Base catalysts for the alkylation the aldehyde by a trihaloacetic acid include, but are not limited to, sodium trichloroacetate, sodium hydride, sodium hydroxide, and sodium methoxide. Preferred is sodium trichloroacetate. It is understood that the concentration of base catalyst is about equivalent to the concentration of the trichloroacetic acid.

It is understood that tribromoacetic acid, or any other analogue, can be substituted for trichloroacetic acid in this reaction. It is also understood that the reaction is generally applicable to a large scope of substitutents in the cyclopropyl position as exemplified below.

Suitable temperature for the alkylation reaction ranges from the freezing point to refluxing temperature of the nonaqueous solvent, a condition readily determined by one skilled in the art of organic synthesis. It is preferred, for handling purposes, to run the reaction with an internal temperature below 35° C. during addition. It is more preferred to run the reation at room temperature.

It is understood that one skilled in the art can determine the preferred reaction time of Step 1 as dependent on temperature, base catalyst and nonaqueous solvent. Generally, the reaction time is about 1 to about 12 hours. The preferred reaction time is about 1 to about 4 hours.

Step 2. Protection of the Carbinol

This step comprises the protection of the carbinol OH with an alcohol protecting group by contacting the carbinol with an alcohol protecting agent in the presence of a coupling catalyst and an acid scavenger. By way of general guidance, one equivalent of trichlorocarbinol, about 1 to about 2 equivalents, preferably 1.5 equivalents, of an acid scavenger, and about 0.1 to about 0.5 equivalents, preferably about 0.3 equivalents, of a coupling catalyst are dissolved in a suitable nonaqueous solvent at a suitable temperature. To this solution, while stirred, is added about 1.0 equivalents of an alcohol protecting agent, preferably in one portion, and stirred for about one to four, preferably about 1.5 to about 2 hours. After this period of time, generally, the TLC (hexane/ ethylacetate, 4:1 v/v) indicates completion of the reaction. The product, 3a, is provided by work up. Examples of standard work up are shown in Examples 1 and 2. Isolation of the trichlorocarbinol is preferred but not necessary. Purification of the crude product can be done by recrystalization in a 4:1 mixture hexane ethylacetate.

It is preferred that the reaction vessel is dried (for example by heat-air-gun or oven) and equipped with mechanical stirrer, nitrogen inlet and an outlet connected to a bubbler.

Preferred coupling catalysts for step (2) are 1,4-diazabicyclo[2.2.2]octane and dimethylaminopyridine. Most preferred is 1,4-diazabicyclo[2.2.2]octane.

Preferred acid scavengers for Step (2) are any base which will neutralize HCl or HBr produced in the reaction. Preferred acid scavengers are organic bases, more specifically tertiary amines: for example, triethylamine, tributylamine, triisopropylamine, N-methylmorpholine, pyridine, N,N-dimethylaniline, and N,N-diethylaniline. More preferred is triethylamine.

Alcohol protecting agents suitable for this step are sulfonyl chlorides, sulfonyl anhydrides, acid chlorides and anhydrides. Preferred alcohol protecting agents are toluenesulfonyl chloride, toluenesulfonyl anhydride, methylsulfonyl chloride, methylsulfonyl anhydride, acetyl chloride and acetyl anhydride. More preferred are the sulfonyl hydroxy protecting group agents toluenesulfonyl chloride and methylsulfonyl chloride.

Suitable nonaqueous solvents for step (2) are nonprotic solvents such as halogenated solvents, ether solvents, hydrocarbon or aromatic solvents including acetonitrile, but not amides. Preferred solvents include methylenechloride, tetrahydrofuran (THF), diethylether, toluene, xylene, acetonitrile, and dimethylformamide (DMF). More preferred is methylenechloride.

The concentration of carbinol in the solvent may range from about 0.5 molar to about 5.0 molar. Preferred is 0.5 molar to 2.0 molar; more preferred is 1.0 molar.

It is understood that the reaction is generally applicable to a large scope of substitutents in the cyclopropyl position as exemplified below.

Step 3: Elimination: Preparation of Cyclopropylacetylene

This step comprises the elimination by dehalogenation of OH protected cyclopropyltrichlorocarbinol, 3a, to form cyclopropylacetylene. By way of general guidance, one equivalent of an OH protected trichlorocarbinol (3a) is dissolved in a suitable solvent. To this solution, while stirring at a suitable temperature, is added about 3 to about 5 equivalents, preferably about 3.5 equivalents of a strong base, preferably dropwise, preferably by additional funnel. After addition is complete, the reaction mixture is slowly warmed to a temperature below the boiling point of alkyne, preferably about 0° C. to room temperature, more preferably about 0° C. A simple way to monitor the reaction progress is by disappearance of compound 3a on TLC (hexane/ethyl acetate, 4:1). The alkyne product, 4a, is provided by work up. Examples of standard work up are shown in Examples 1 and 2. Crude alkyne is obtained in excellent yield. Simple distillation is preferred to purify the alkyne.

It is preferred that the reaction vessel is dried (for example by heat-air-gun or oven) and equipped with mechanical stirrer, additional funnel, nitrogen inlet and an outlet connected to a bubbler.

Suitable nonaqueous solvents for step (3) are nonprotic solvents such as nonhalogenated solvents, ether solvents, hydrocarbon or aromatic solvents, including acetonitrile and dimethylsulfoxide. Preferred solvents when organometallic reagents are employed as the strong base include tetrahydrofuran, diethylether, dimethylsulfoxide, 1,4-dioxane, acetonitrile, N-methylpyrolidinone, heptane, hexanes, and toluene. Generally, more preferred is tetrahydrofuran. When sodium amide is the strong base DMSO is more preferred. Additionally, it is preferred that the solvent is dry.

Suitable temperature for the elimination reaction ranges from about −30° C. to about 10° C. for the addition of the strong base, more preferably about −30° C. to about 0° C., even more preferably about about −30° C. to about −20° C., a condition readily determined by one skilled in the art of organic synthesis. After addition of the strong base it is preferred, for handling purposes, to run the reaction with an internal temperature below the boiling point of alkyne being formed, preferably about 0° C. to room temperature, more preferably about 0° C. It is more preferred to run the reaction at about 0° C.

Strong bases for step (3) are organometallic bases such as metal amides, alkyl lithiums, and grignard reagents. Such strong bases include sodium amide, potassium amide, lithium amide, lithium diisopropylamide, methyllithium, butyllithium, hexyllithium, phenyllithium, and butyl magnesium chloride. Preferred bases are sodium amide, potassium amide, lithium amide, and methyllithium; more preferred is sodium amide and methyllithium.

The concentration of OH protected cyclopropyltrichlorocarbinol, 3a, in the solvent may range from about 0.5 molar to about 5.0 molar. Preferred is 0.5 molar to 3.0 molar; more preferred is 1.0 to 2.0 molar.

It is understood that the reaction is generally applicable to a large scope of substitutents in the cyclopropyl position as exemplified below.

The methods of the present invention, by way of example and without limitation, may be further understood by reference to Scheme 3. Scheme 3 details the improved general synthetic method for synthesis of $R^1$ substituted acetylenes by the present invention wherein alkylation of cyclopropyl carboxaldehyde by a dihalo —$CR^{2a}R^{2b}R^{2c}$ anion is generated from dichloromethane, or optionally dibromomethane.

Scheme 3

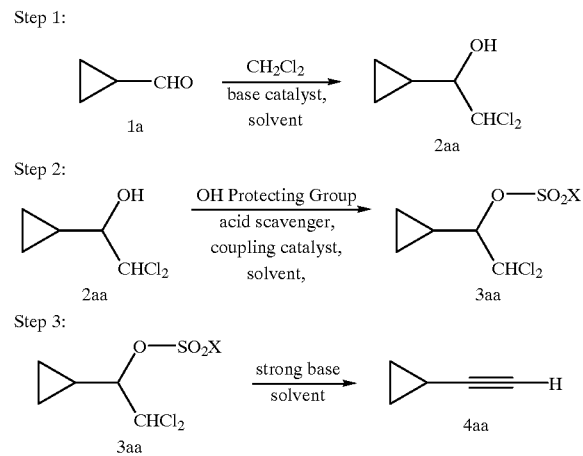

Step 1. Alkylation of Cyclopropylcarboxaldehyde

This step is conducted by reacting cyclopropyl carboxaldehyde in a suitable nonaqueous solvent at a suitable temperature with dichloromethane in the presence of a suitable base catalyst to form cyclopropyldichlorocarbinol of formula 2aa. By way of general guidance, a reaction vessel is charged with a nonaqueous solvent, about 1.5 to about 5 equivalents, preferably about 2 to about 4 equivalents, more preferably 2.5 to 3 equivalents of dichloromethane and about one equivalent of aldehyde. To this solution, while stirring at a suitable temperature, is added a base catalyst (about 1.2 to about 2.0 equivalents, preferably 1.5 eq) portionwise, preferably dropwise, over a period of 5 minutes to one hour. After addition is complete, the solution is stirred at a suitable temperature for preferably about 2 hours. The product, 2aa, can be isolated by work up. Examples of standard work up are shown in Examples 10 and 11. Isolation of the dichlorocarbinol is preferred but not necessary. The crude dichlorocarbinol is obtained in good purity such that purification of the dichlorocarbinol is generally not needed.

It is preferred that the reaction vessel is dried (for example by heat-air-gun or oven) and equipped with mechanical stirrer, an addition funnel, nitrogen inlet and an outlet connected to a bubbler. It is further preferred that the atmosphere and conditions of the reaction be dry, inert and/or nonaqueous.

Suitable nonaqueous solvents are nonprotic solvents which do not react with the strong base, such as ether solvents or aromatic solvents. Preferred solvents include tetrahydrofuran, toluene, diethylether, 1,4-dioxane, toluene, hexanes, and heptane. More preferred is tetrahydrofuran. Furthermore, it is preferred, but not necessary, that the solvent be dry.

The concentration of aldehyde in the solvent may range from about 0.5 molar to about 4.0 molar. Preferred is about 0.5 molar to about 2.0 molar; more preferred is about 1.0 molar.

Base catalysts for the alkylation of the aldehyde by dichloromethane include, but are not limited to, lithium amide, lithium dialkyl amides and metal alkoxides. Preferred is lithium diisopropyl amide, KHMDA, LiHMDA, sodium amide, potassium amide, as well as, sodium methoxide and sodium ethoxide. More preferred is lithium diisopropyl amide. It is understood that the concentration of base catalyst is about equivalent to the concentration of the dichloromethane.

It is understood that dibromomethane may be substituted for dichloromethane in this reaction. It is also understood that the reaction is generally applicable to a large scope of substitutents in the cyclopropyl position as exemplified below.

Suitable temperature for the addition of base catalyst in the alkylation reaction ranges from the freezing point to −50° C. of the nonaqueous solvent, preferably, −78° C. to −60° C. After addition of the base catalyst, the temperature is preferably maintained between −78° C. and −60° C. If dibromomethane is used instead of dichloromethane, a suitable temperature for the addition of base catalyst ranges from the freezing point to −25° C. of the nonaqueous solvent, preferably, −35° C. to −25° C. After addition of the base catalyst, the temperature is preferably maintained between −35° C. and 5° C.

It is understood that one skilled in the art can determine the preferred reaction time of Step 1 as dependent on temperature, base catalyst and nonaqueous solvent. Generally, the reaction time is about 1 to about 12 hours. The preferred reaction time is about 1 to about 4 hours.

Step 2. Protection of the Carbinol

This step comprises the protection of the dichlorocarbinol OH with an alcohol protecting group by contacting the dichlorocarbinol with an alcohol protecting agent in the presence of an acid scavenger and optionally a coupling catalyst. By way of general guidance, one equivalent of dichlorocarbinol, about 1 to about 2 equivalents, preferably 1.5 equivalents, of an acid scavenger, and optionally, about 0.1 to about 0.5 equivalents, preferably about 0.3 equivalents, of a coupling catalyst are dissolved in a suitable nonaqueous solvent at about 0° C. to room temperature. To this solution, while stirred, is added about 1.0 to about 1.5 equivalents of an alcohol protecting agent, preferably in one portion, and stirred for about one to four, preferably about 1.5 to about 2 hours at preferably room temperature. After this period of time, generally, the TLC (hexane/ethylacetate, 4:1 v/v) indicates completion of the reaction. The product, 3aa, is provided by work up. Examples of standard work up are shown in Examples 10 and 11. Isolation of the protected diichlorocarbinol is preferred but not necessary. Purification of the crude product can be done by recrystalization in a 4:1 mixture hexane ethylacetate.

It is preferred that the reaction vessel is dried (for example by heat-air-gun or oven) and equipped with mechanical stirrer, nitrogen inlet and an outlet connected to a bubbler.

Preferred coupling catalysts for step (2), when used, are 1,4-diazabicyclo[2.2.2]octane and dimethylaminopyridine. Most preferred is 1,4-diazabicyclo[2.2.2]octane. However, the presence of the coupling catalyst is optional and not required.

Preferred acid scavengers for Step (2) are any base which will neutralize HCl or HBr produced in the reaction. Preferred acid scavengers are organic bases, more specifically tertiary amines: for example, triethylamine, tributylamine, triisopropylamine, diisopropylmethylamine, N-methylmorpholine, pyridine, N,N-dimethylaniline, and N, N-diethylaniline. More preferred is triethylamine.

Alcohol protecting agents suitable for this step are sulfonyl chlorides, sulfonyl anhydrides, acid chlorides and anhydrides. Preferred alcohol protecting agents are toluenesulfonyl chloride, toluenesulfonyl anhydride, methylsulfonyl chloride, methylsulfonyl anhydride, acetyl chloride and acetyl anhydride. More preferred are the sulfonyl hydroxy protecting group agents toluenesulfonyl chloride and methylsulfonyl chloride. Most preferred is toluenesulfonyl chloride.

Suitable nonaqueous solvents for step (2) are nonprotic solvents such as halogenated solvents, ether solvents, hydrocarbon or aromatic solvents including acetonitrile. Preferred solvents include methylenechloride, tetrahydrofuran, acetonitrile, diethylether, toluene, 1,4-dioxane, heptane, and hexanes. More preferred is methylenechloride.

The concentration of carbinol in the solvent may range from about 0.5 molar to about 5.0 molar. Preferred is 0.5 molar to 2.0 molar; more preferred is 1.0 molar.

It is understood that the reaction is generally applicable to a large scope of substitutents in the cyclopropyl position as exemplified below.

Step 3: Elimination: Preparation of Cyclopropylacetylene

This step comprises the elimination by dehalogenation of OH protected cyclopropyldichlorocarbinol, 3aa, to form cyclopropylacetylene. By way of general guidance, one equivalent of an OH protected dichlorocarbinol (3aa) is dissolved in a suitable solvent. To this solution, while stirring at a suitable temperature, is added about 2 to about 5 equivalents, preferably about 2.5 equivalents of a strong base dropwise, preferably by additional funnel. After addition is complete, the reaction mixture is slowly warmed to a temperature below the boiling point of alkyne, preferably about 0° C. to room temperature, more preferably about 0° C. A simple way to monitor the reaction progress is by disappearance of compound 3aa on TLC (hexane/ethyl acetate, 4:1). The alkyne product, 4aa, is provided by work up. Examples of standard work up are shown in Examples 10 and 11. Crude alkyne is obtained in excellent yield. Simple distillation is preferred to purify the alkyne.

It is preferred that the reaction vessel is dried (for example by heat-air-gun or oven) and equipped with mechanical stirrer, additional funnel, nitrogen inlet and an outlet connected to a bubbler.

Suitable nonaqueous solvents for step (3) are nonprotic solvents such as nonhalogenated solvents, ether solvents, hydrocarbon or aromatic solvents, including acetonitrile and dimethylsulfoxide. Preferred solvents when organometallic reagents are employed as the strong base include tetrahydrofuran, diethylether, dimethylsulfoxide, 1,4-dioxane, acetonitrile, N-methylpyrolidinone, heptane, hexanes, and toluene. Generally, more preferred is tetrahydrofuran. When sodium amide is the strong base DMSO is more preferred. Additionally, it is preferred that the solvent is dry.

Suitable temperature for the elimination reaction ranges from about −30° C. to about 10° C. for the addition of the strong base, more preferably about −30° C. to about 0° C., even more preferably about about −30° C. to about −20° C., a condition readily determined by one skilled in the art of organic synthesis. After addition of the strong base it is preferred, for handling purposes, to run the reaction with an internal temperature below the boiling point of alkyne being formed, preferably about 0° C. to room temperature, more preferably about 0° C. It is more preferred to run the reaction at about 0° C.

Strong bases for step (3) are organometallic bases such as metal amides, alkyl lithiums, and grignard reagents. Such strong bases include sodium amide, potassium amide, lithium amide, lithium diisopropylamide, methyllithium, butyllithium, hexyllithium, phenyllithium, and butyl magnesium chloride. Preferred bases are sodium amide, potassium amide, lithium amide, and methyl lithium; more preferred is sodium amide or methyl lithium.

The concentration of OH protected cyclopropyltrichlorocarbinol, 3aa, in the solvent may range from about 0.5 molar to about 5.0 molar. Preferred is 0.5 molar to 3.0 molar; more preferred is 1.0 to 2.0 molar.

It is understood that the reaction is generally applicable to a large scope of substitutents in the cyclopropyl position as exemplified below.

The following examples are meant to be illustrative of the present invention. These examples are presented to exemplify the invention and are not to be construed as limiting the invention's scope.

EXAMPLE 1

General Procedure for Preparation of Trichlorocarbinols

A heat-air-gun dried, 3 L, three neck round-bottomed flask equipped with mechanical stirrer, nitrogen inlet and an outlet connected to a bubbler, is charged with a solution of trichloroacetic acid (1.5 mols, 1.5 eq) in DMF (700 mL). The aldehyde (1 mol, 1 eq.) is added into it with continues $N_2$ flow. Then, to this stirred solution is added sodium trichloroacetate (1.5 mols, 1.5 eq.) portionwise, keeping the internal temperature below 35° C. during addition. The $N_2$ flow is stopped and the heterogeneous mixture is stirred at room temperature for 2 hours with continues evolution of $CO_2$. Generally, the reaction can be monitored by $^1$H-NMR indicating the reaction completion by total disappearing of the aldehyde proton signal. The reaction mixture was cooled to 5° C. and carefully quenched with water (250 mL). A thick emulsion is formed which is diluted with water (1000 mL) and extracted with hexanes (3×500 mL). The combined organic phases are washed with water (500 mL) and a saturated aqueous solution of ammonium chloride (500 mL). The organic phase is dried over $MgSO_4$ anhydrous, filtered and concentrated by rotary evaporation. The crude trichlorocarbinol is obtained in relative good purity but it can be purified by flash chromatography or distillation.

General Procedure for Tosylation of Trichlorocarbinols

In a dried, 500 mL, round-bottomed flask equipped with a magnetic stirrer and under nitrogen is dissolved the trichlorocarbinol (0.1 mols), triethylamine (0.15 mols, 1.5 eq) and dabco® (0.03 mols, 0.3 eq) in methylenechloride (200 mL) at room temperature. To this stirred solution at room temperature is added toluenesulfonylchloride (0.1 mols, 1 eq) in one portion, and stirred for additional two hours. After this period of time, generally, the TLC (hexane/ethylacetate, 4:1 v/v) indicates completion of the reaction. The reaction is quenched with water (50 mL). The organic phase in successively washed with HCl (5 M, 100 mL), water (100 mL). The combine aqueous phase is extracted with $CH_2Cl_2$ (2×100 mL). The organic phases are combined and washed with an aqueous solution of NaOH (2 M, 200 mL), water (100 mL) and finally brine (100 mL). This solution is dried over $MgSO_4$, filtered and concentrated to afford trichlorotosylate as a solid. Purification of the crude product can be done by recrystalization in a 4:1 mixture hexane ethylacetate.

General Procedure for Methanesulfonylation of Trichlorocarbinols

This preparation is a typical example for this procedure: In a oven dried, 500 mL, round-bottomed flask equipped with a magnetic stirrer and under nitrogen is dissolved the trichlorocarbinol (0.1 mols), triethylamine (0.15 mols, 1.5 eq) and dabco® (0.03 mols, 0.3 eq) in methylenechloride (200 mL) at room temperature. To this stirred solution at room temperature is added methanesulfonylchloride (0.1 mols, 1 eq) in one portion, and stirred for additional 1.5 hours. After this period of time, generally, the TLC (hexane/ethylacetate, (4:1), $R_f$=0.75) indicates completion of the reaction (depending upon substrate). The reaction is quenched with water (50 mL). The organic phase in successively washed with HCl (5 M, 100 mL), water (100 mL). The combine aqueous phase is extracted with $CH_2Cl_2$ (2×100 mL). The organic phases are combined and washed with an aqueous solution of NaOH (2 M, 200 mL), water (100 mL) and finally brine (100 mL). This solution is dried over $MgSO_4$, filtered and concentrated to afford trichlorotosylate as a solid. Purification of the crude product can be done by recrystalization in a 4:1 mixture hexane ethylacetate.

General Procedure for Preparation of Acetylene

In an oven dried, 500 mL, three neck round-bottomed flask equipped with a magnetic stirrer, additional funnel and a nitrogen inlet is dissolved the trichlorotosylate (10 mmols, 1 eq) in dried THF (100 mL). To this stirred solution at −30° C. is added MeLi (1.4 M in ether, 35 mmols, 3.5 eq) dropwise via additional funnel. After addition is completed, the reaction mixture is allowed to slowly warm to 0° C. in a period of one hour. A simple way to monitor the reaction progress is by despairing of the tosylate on TLC (hexane/ethyl acetate, 4:1). The reaction is quenched with saturated aqueous solution of ammonium chloride (50 mL) and diluted with t-butyl methyl ether (100 mL). The aqueous phase is extracted with t-butyl methyl ether (3×50 mL). The combine organic phase is washed with brine (100 mL) and dried over $MgSO_4$ anhydrous. After filtration and condensation crude acetylene is obtained in excellent yield. A simple distillation is recommended to purify the acetylene. The characterization of all acetylene derivatives by comparison with commercially available authentic samples.

EXAMPLE 2

Preparation of Cyclopropylacetylene

Step 1: 1,1,1-trichloro-2-cyclopropylethanol

This preparation is a typical example of this procedure. To a stirred solution of trichloroacetic acid (960.7 g, 5.88 mols), cyclopropylcarboxaldehyde (275.0 g, 3.92 mols) in DMF (2.5 L) at 25° C. was added sodium trichloroacetate (1090 g, 5.88 mols) portionwise. The internal temperature was kept below 35° C. by addition control. After addition was completed, the mixture was stirred at room temperature for 4 hours with continuous evolution of $CO_2$. The reaction was monitored by $^1$H-NMR using despairing of aldehyde proton signal. After this period of time, a very dark solution is observed and the reaction is completed. The solution was cooled to 5° C. and carefully quenched with water (2 L). The decomposition of sodium trichloroacetate excess may be violent and fizzing. After reaction mixture was quenched, the heterogeneous emulsion was diluted with water (4 L) and extracted with hexane (3×1 L). The combined organic solution was washed with water (1 L) and a saturated aqueous solution of ammonium chloride (1 L). The organic phase was dries over $MgSO_4$, filtered and rotary evaporated to afford 699.0 g (94%) of 1,1,1-trichloro-2- cyclopropylethanol as a dark oil. No purification was needed for further steps. b.p.: 45°–47° C./8 torr. TLC: hexane/ethylacetate, (4:1), $R_f$=0.55.$^1$H-NMR δ(CDCl$_3$): 6.42 (m, 3H), 1.75–1.80 (m, 1H), 1.32 (m, 1H), 3.58 (d, J=10.0 Hz). $^{13}$C-NMR δ(CDCl$_3$): 2.02, 5.82, 13.0, 85.82, 104.0 ppm. MS(CI/NH$_3$): (M+1): 190.

Step 2: 1,1,1-trichloro-2-cyclopropyl-2-ethyltosylate

This preparation is a typical example for this procedure:
To a stirred solution of 1,1,1-trichloro-2-cyclopropylethanol (0.211 mols, 1 eq), triethylamine (0.317 mols, 1.5 eq) and dabco® (0.063 mols, 0.3 eq) in methylenechloride (400 mL) at room temperature, was added toluenesulfonylchloride (0.211 mols, 1 eq) in one portion. The solution was stirred for 1.5 hours at room temperature. The reaction was quenched with water (150 mL). The organic phase was successively washed with HCl (5 M, 150 mL), water (150 mL). The combine aqueous phase was extracted with CH$_2$Cl$_2$ (2×150 mL). The organic phases were combined and washed with an aqueous solution of NaOH (2 N, 300 mL), water (150 mL) and finally brine (150 mL). This solution was dried over MgSO$_4$, filtered and concentrated by rotary evaporator to obtained 1,1,1-trichloro-2-cyclopropyl-2-ethyltosylate. Purification of the crude product by recrystalization using a 4:1 mixture hexane/ethyl acetate to afford 66.1 g (91%). m.p.: 74°–75° C. $^1$H-NMR δ(CDCl$_3$): 0.62–0.95 (m, 4H), 1.20–1.32 (m, 1H), 2.45 (s, 3H), 4.55 (d, J=11.4 Hz), 7.32 (d, J=9.9 Hz, 2H), 7.82 (d, J=9.90, 2H). $^{13}$C-NMR δ(CDCl$_3$): 3.09, 7.82, 12.90, 21.05, 92.05, 99.02, 126.8, 129.9, 134.5, 145.0 ppm. MS(CI/NH$_3$): (M+1): 344. C$_{12}$H$_{13}$Cl$_3$O$_3$S: theo. C: 41.94%, H: 3.81%, S 9.33%; found: C: 41.97%, H: 3.77%, S: 9.33%.

Alternative Step 2: 1,1,1-trichloro-2-cyclopropyl-2-ethylmethanesulfonylate

To a stirred solution of 1,1,1-trichloro-2-cyclopropylethanol (250 g, 1.319 mols, leq), triethylamine (276 mL, 1.979 mols, 1.5 eq) and dabco® (0.063 mols, 0.3 eq) in methylenechloride (1000 mL) at 0° C., was added methanesulfonylchloride (112.3 mL, 1.451 mols, 1.1 eq) in one portion. The solution was allowed to warm up to 25° C. and stirred for 1.5 hours. The reaction was quenched with water (150 mL). The organic phase was successively washed with HCl (5 M, 150 mL), water (150 mL). The combine aqueous phase was extracted with CH$_2$Cl$_2$ (2×150 mL). The organic phases were combined and washed with an aqueous solution of NaOH (2 N, 300 mL), water (150 mL) and finally brine (150 mL). This solution was dried over MgSO$_4$, filtered and concentrated by rotary evaporator to obtained 1,1,1-trichloro-2-cyclopropyl-2-ethylmethanesulfonylate Purification of the crude product by recrystalization using a 4:1 mixture hexane/ethyl acetate to afford 324.7 g (92%). m.p.: 46.3°–48.6° C. $^1$H-NMR δ(CDCl$_3$): 0.78–0.92 (m, 3H), 0.97–1.02 (m, 1H), 1.45 (m, 1H), 3.21 (s, 3H), 4.50 (d, J=11.4 Hz). $^{13}$C-NMR δ(CDCl$_3$): 3.89, 7.72, 11.34, 39.85, 92.05, 98.02 ppm. MS(CI/NH$_3$): (M+1): 268. C$_6$H$_9$Cl$_3$O$_3$S: theo. C: 26.94%, H: 3.39%, S 11.99%; found: C: 26.94%, H: 3.42%, S: 12.03%.

Alternative Step 2: 1.1,1-trichloro-2-cyclopropylethyl acetate

To a stirred solution of 1,1,1-trichloro-2-cyclopropylethanol (100 g, 0.528 mols, 1 eq) and triethylamine (110 mL, 0.792 mols, 1.5 eq) in methylenechloride (500 mL) at 0° C., was added acetyl chloride (41.3 mL, 0.581 mols, 1.1 eq) in one portion. The solution was allowed to warm up to 25° C. and stirred for 1 hour. The reaction was quenched with water (150 mL). The organic phase was successively washed with HCl (5 M, 150 mL), water (150 mL). The combine aqueous phase was extracted with CH$_2$Cl$_2$ (2×150 mL). The organic phases were combined and washed with an aqueous solution of NaOH (2 N, 300 mL), water (150 mL, pH≈7) and finally brine (150 mL). This solution was dried over MgSO$_4$, filtered and concentrated by rotary evaporator to obtained 1,1,1-trichloro-2-cyclopropyl-2-cyclopropylethyl acetate. Purification of the crude product by recrystalization using a 4:1 mixture hexane/ethyl acetate to afford 101.0 g (98%). $^1$H-NMR δ(CDCl$_3$): 0.54–0.78 (m, 3H), 0.82–0.92 (m, 1H), 1.43 (m, 1H), 2.18 (s, 3H), 4.87 (d, J=11.4 Hz). $^{13}$C-NMR δ(CDCl$_3$): 2.21, 6.22, 12.34, 21.43, 84.05, 98.92 ppm. MS(CI/NH$_3$): (M+1): 195. C$_7$H$_9$Cl$_3$O$_3$S.

Step 3: Cyclopropylacetylene (CPA)

This preparation is a typical example for this procedure:
To a stirred solution of 1,1,1-trichloro-2-cyclopropyl-2-ethyltosylate (29.10 mmol) in dried THF (290 mL) at −30° C. was added MeLi (1.4 M in ether, 101.9 mmol) dropwise via additional funnel. After the addition was completed, the solution was allowed to slowly warm to 0° C. in one hour period. At this time, TLC (hexane/ethyl acetate, 4:1) indicated no starting material left. The reaction was quenched with saturated aqueous solution of ammonium chloride (120 mL) and diluted with ethyl acetate (250 mL). The aqueous phase is extracted with ethyl acetate (3×100 mL). The combine organic phase is washed with brine (150 mL) and dried over MgSO$_4$ anhydrous. After filtration, 94% solution yield of CPA in THF/ethyl acetate was obtained. Neat CPA can be distilled (b.p. 52° C./760 torr) by using vacuum at room temperature and condensing it in a CO$_2$/acetone trap, which afford 1.78 g (89%) of neat CPA.

Alternative Step 3

To a four necked round bottom flask equipped with a magnetic stirrer, a nitrogen outlet, and an efficient outlet connected to a bubbler, NaNH$_2$ (113.7 g, 2.91 mol, 5 eq.) was suspended in 850 ml of DMSO (caution: severe NH$_3$ gas releasing was observed) and warmed to 40° C. under vigorous stirring to form a homogeneous solution. The solution was then cooled to 5° C. To the solution, cyclopropyl trichlorocarbinol tosylate (200 g, 0.58 mol, 1 eq.) dissolved in 200 ml of DMSO was added slowly via addition funnel (in such a rate that internal temperature was not exceeding 20° C.) in 75 minutes. The reaction was stirred at 15° C. to 20° C. for 15 minutes after the addition. The reaction mixture was then cooled to 5° C. To the solution, water (60 g, 3.3 mol, 5.7 eq) was added slowly (in such a rate that internal temperature was not exceeding 20° C.) in 20 minutes. After the addition, the reaction mixture was stirred at room temperature for 5 minutes. The neat CPA (30.7 g, 80.1% yield) was obtained by direct distillation under reduced pressure.

EXAMPLE 3

Preparation of 3,3-dimethyl-1-butyne

The title compound was prepared according to Scheme 2 using the procedures of Example 1 and/or 2 starting from trimethylacetaldehyde. The product, 4e, was compared to an authentic reference, the yield is listed in Example 9.

Compound 2e: 1,1,1-trichloro-3,3-dimethyl-2-butanol: Yield: 89%. $^1$H-NMR δ(CDCl$_3$): 1.21 (s, 9H), 3.05 (s, broad, 1H), 3.87 (s, 1H). $^{13}$C-NMR δ(CDCl$_3$): 28.22 (tert-butyl, 3C), 37.82, 87.88, 104.0 ppm. MS(CI/NH$_3$) (M+1): 206

Compound 3e; 1,1,1-trichloro-3,3-dimethyl-2-butylmethanesulfonylate: Yield: 68%. m.p.: 61.5°–63° C. $^1$H-NMR δ(CDCl$_3$): 1.31 (s, 9H), 3.25 (s, 3H), 5.07 (s, 1H). $^{13}$C-NMR δ(CDCl$_3$): 28.22 (tert-butyl, 3C), 87.88, 94.0 ppm. MS(CI/NH$_3$) (M+1): 284. C$_7$H$_{13}$Cl$_3$O$_3$S: theo. : C:29.65%, H: 4.62%, S: 11.31%. found: C: 29.82%, H: 4.70%, S: 11.52%.

EXAMPLE 4

Preparation of Cyclohexylacetylene

The title compound was prepared according to Scheme 2 using the procedures of Example 1 and/or 2 starting from cyclohexanecarboxaldehyde. The product, 4b, was compared to an authentic reference, the yield is listed in Example 9.

Compound 2b; 1,1,1-trichloro-2-cyclohexylethanol: Yield: 94%. $^1$H-NMR δ(CDCl$_3$): 1.05–1.40 (m, 5H), 1.72–1.82 (m, 5H), 2.94 (m, 1H), 3.33 (d, J=5.2 Hz). $^{13}$C-NMR δ(CDCl$_3$): 21.80, 25.70, 25.87, 26.02, 28.00, 33.02, 40.05, 92.00, 99.80 ppm. MS(CI/NH$_3$) (M+1): 233
Compound 3b;1,1,1-trichloro-2-cyclohexylethyltosylate: Yield: 78%. m.p.: 117.5°–118° C. $^1$H-NMR δ(CDCl$_3$): 1.05–1.38 (m, 5H), 1.45–1.62 (m, 2H), 1.78–1.88 (m, 2H), 2.0(d, J=9.2 Hz, 1H), 2.10–2.22 (m, 1H), 2.45 (s, 3H), 4.80 (d, J=8.3 Hz, 1H), 7.35 (d, J=11.8 Hz, 2H), 7,82 (d, J=11.6 Hz, 2H). $^{13}$C-NMR δ(CDCl$_3$): 21.80, 25.70, 25.87, 26.02, 28.00, 33.02, 40.05, 92.00, 99.80, 122.4, 128.0, 129.8, 134.0, 145.6 ppm. MS(CI/NH$_3$) (M+1): 387. C$_{15}$H$_{19}$Cl$_3$O$_3$S: theo. : C: 46.71%, H: 4.96%, S: 3.31%; found: C: 46.65%, H: 5.01%, S: 8.28%.

EXAMPLE 5

Preparation of Phenylacetylene

The title compound was prepared according to Scheme 2 using the procedures of Example 1 and/or 2 starting from benzaldehyde. The product, 4f, was compared to an authentic reference, the yield is listed in Example 9.
Compound 2f; 1,1,1-trichloro-2-phenylethanol: Yield: 90% $^1$H-NMR δ(CDCl$_3$): 5.20 (s, 1H), 7.37–7.39 (m, 3H), 7.62 (m, 2H). $^{13}$C-NMR δ(CDCl$_3$): 21.90, 85.32, 99.00, 127.8, 129.9, 131.0, 143.2 ppm. MS(CI/NH$_3$) (M+1): 226
Compound 3f; 1,1,1-trichloro-2-phenylethyltosylate: Yield: 75%. m.p.: 126.3°–127.6° C. $^1$H-NMR δ(CDCl$_3$): 2.35 (s, 3H), 5.85 (s, 1H), 7.12–7.32 (m, 5H), 7.42 (d, J=8.3 Hz, 2H), 7.60 (d, J=8.3 Hz, 2H). $^{13}$C-NMR δ(CDCl$_3$): 21.90, 46.02, 52.00, 88.77, 99.00, 127.8, 129.9, 131.0, 143.2, 122.4, 128.0, 129.8, 134.0, 145.6 ppm. MS(CI/NH$_3$) (M+1): 381. C$_{15}$H$_{13}$Cl$_3$O$_3$S: theo. : C: 47.45%, H: 3.45%, S: 8.45%. found: C: 47.51%, H: 3.47%, S: 8.44%.

EXAMPLE 6

Preparation of 4-methyl-1-pentyne

The title compound was prepared according to Scheme 2 using the procedures of Example 1 and/or 2 starting from isovaleraldehyde. The product, 4c, was compared to an authentic reference, the yield is listed in Example 9.
Compound 2c; 1,1,1-trichloro-3-methyl-2pentanol: Yield: 88%. $^1$H-NMR δ(CDCl$_3$): 0.90 (d, J=9.8 Hz, 3H), 1.04 (d, J=9.8 Hz, 3H), 2.65–2.72 (m, 1H), 2.82–2.95 (m, 2H), 4.10 (dd, 1H). $^{13}$C-NMR δ(CDCl$_3$): 21.00, 21.80, 23.80, 24.0, 40.90, 80.67, 99.00 ppm. MS(CI/NH$_3$) (M+1): 206
Compound 3c; 1,1,1-trichloro-3-methyl-2-pentyltosylate:
Yield: 89%. m.p.: 118°–120° C. $^1$H-NMR δ(CDCl$_3$): 0.94 (d, J=10.0 Hz, 3H), 1.05 (d, J=9.8 Hz, 3H), 1.82–1.95 (m, 3H), 4.05 (s, 3H) 5.18 (d, J=6.8 Hz, 1H), 4.55, 7.35 (d, J=9.8 Hz, 2H), 7.82 (d, J=9.8 Hz, 2H) $^{13}$C-NMR δ(CDCl$_3$): 21.00, 21.80, 23.80, 24.0, 40.90, 52.0, 80.77, 99.00, 117.5, 127.8, 129.7, 134.0, 145.0 ppm. MS(CI/NH$_3$) (M+1): 361. C$_{13}$H$_{17}$Cl$_3$O$_3$S: theo.: C: 43.41%, H: 4.76%, S: 8.92%. found: C: 43.36%, H: 4.81%, S: 8.88%.

EXAMPLE 7

Preparation of 4-phenyl-1-butyne

The title compound was prepared according to Scheme 2 using the procedures of Example 1 and/or 2 starting from 3-phenyl-propionaldehyde. The product, 4 g, was compared to an authentic reference, the yield is listed in Example 9.
Compound 2c; 1,1,1-trichloro-4-phenyl-2-butanol: Yield:89%. $^1$H-NMR δ(CDCl$_3$): 2.18–2.30 (m, 2H), 2.80–3.0 (m, 2H), 4.08 (dd, 1H). $^{13}$C-NMR δ(CDCl$_3$): 21.90, 31.80, 33.90, 88.7, 98.30 ppm. MS(CI/NH$_3$) (M+1): 254
Compound 3c; 1,1,1-trichloro-4-phenyl-2-butyltosylate: Yield: 82%. m.p.: 85.3°–86.2° C. $^1$H-NMR δ(CDCl$_3$): 2.18–2.30 (m, 1H) 2.42 (s, 3H), 2.53 (m, 1H), 2.74–2.92 (m, 2H), 5.10 (dd, 1H), 7.17–7.35 (m, 7H), 7.84 (d, J=9.8 Hz, 2H). $^{13}$C-NMR δ(CDCl$_3$): 21.90, 31.80, 33.90, 88.7, 98.30, 126.4, 128.6, 128.8, 127.2, 128.4, 129.8, 134.0, 140.0, 145.0 ppm. MS(CI/NH$_3$) (M+1): 409. C$_{17}$H$_{17}$Cl$_3$O$_3$S: theo.: C: 50.08%, H: 4.20%, S: 7.87%. found.: C: 50.12%, H: 4.22%, S: 7.88%.

EXAMPLE 8

Preparation of 1-Decyne

The title compound was prepared according to Scheme 2 using the procedures of Example 1 and/or 2 starting from nonyl aldehyde. The product, 4d, was compared to an authentic reference, the yield is listed in Example 9.
Compound 2d; 1,1,1-trichloro-2-decanol: Yield: 85%. $^1$H-NMR δ(CDCl$_3$): 0.88 (t, 3H), 1.20–1.45 (m, 10H), 1.90 (m, 2H), 2.15 (m, 2H), 4.22 (dd, J$_1$=7.8, J$_2$=8.4, 1H). $^{13}$C-NMR δ(CDCl$_3$): 14.00, 21.90, 22.12, 25.52, 29.87, 29.92, 31.82, 31.90, 89.20, 99.15 ppm. MS(CI/NH$_3$) (M+1): 292
Compound 3d; 1,1,1-trichloro-2-decanyltosylate: Yield: 90%. $^1$H-NMR δ(CDCl$_3$): 0.88 (t, 3H), 1.19–1.55 (m, 10H), 1.90 (m, 2H), 2.15 (m, 2H), 2.42 (s, 3H), 4.22 (dd, J$_1$=7.8, J$_2$=7.4, 1H), 7.35 (d, J=9.8 Hz, 2H), 7.82 (d, J=9.8 Hz, 2H). $^{13}$C-NMR δ(CDCl$_3$): 14.00, 21.90, 22.12, 25.52, 29.87, 29.92, 31.82, 31.90, 89.20, 99.15, 127.4, 129.7, 129.8, 132.0, 145.6 ppm. MS(CI/NH$_3$) (M+1): 417. C$_{17}$H$_{25}$Cl$_3$O$_3$S: theo.: C: 49.11%, H: 6.06%, S: 7.71%.

EXAMPLE 9

TABLE 1

Compounds prepared by the procedures of Scheme 2.

| Formula | 2 | Yield (%)$^a$ | 3 | Yield (%)$^b$ | 4 | Yield (%)$^c$ |
|---|---|---|---|---|---|---|
| a | cyclopropyl-CH(OH)-CCl$_3$ | 95 | cyclopropyl-CH(OTs)-CCl$_3$ | 91 | cyclopropyl-C≡CH | 94$^d$ |

TABLE 1-continued

Compounds prepared by the procedures of Scheme 2.

| Formula | 2 | Yield (%)[a] | 3 | Yield (%)[b] | 4 | Yield (%)[c] |
|---|---|---|---|---|---|---|
| b | cyclohexyl-CH(OH)-CCl$_2$-Cl | 94 | cyclohexyl-CH(OTs)-CCl$_2$-Cl | 78 | cyclohexyl-C≡CH | 87 |
| c | (CH$_3$)$_2$CHCH$_2$-CH(OH)-CCl$_2$-Cl | 88 | (CH$_3$)$_2$CHCH$_2$-CH(OTs)-CCl$_2$-Cl | 89 | (CH$_3$)$_2$CHCH$_2$-C≡CH | 90[d] |
| d | CH$_3$(CH$_2$)$_7$-CH(OH)-CCl$_2$-Cl | 85 | CH$_3$(CH$_2$)$_7$-CH(OTs)-CCl$_2$-Cl | 90 | CH$_3$(CH$_2$)$_7$-C≡CH | 95 |
| e | (CH$_3$)$_3$C-CH(OH)-CCl$_2$-Cl | 89 | (CH$_3$)$_3$C-CH(OMs)-CCl$_2$-Cl | 68 | (CH$_3$)$_3$C-C≡CH | 81[d] |
| f | C$_6$H$_5$-CH(OH)-CCl$_2$-Cl | 90 | C$_6$H$_5$-CH(OTs)-CCl$_2$-Cl | 75 | C$_6$H$_5$-C≡CH | 89 |
| g | C$_6$H$_5$CH$_2$CH$_2$-CH(OH)-CCl$_2$-Cl | 89 | C$_6$H$_5$CH$_2$CH$_2$-CH(OTs)-CCl$_2$-Cl | 82 | C$_6$H$_5$CH$_2$CH$_2$-C≡CH | 98 |

[a]No purification is needed for next step.
[b]Base on recrystalized product; hexane/ethylacetate (4:1).
[c]Base on isolated yield, otherwise indicated.
[d]Solution yield by GC.

EXAMPLE 10

General Procedure for Preparation of Dichlorocarbinols

An oven dried, 1 L-three neck round-bottomed flask, equipped with a magnetic stirrer, an additional funnel and under nitrogen, is charged with dried THF (200 mL), methylenechloride (0.3 mols, 3 eq.) and the aldehyde (0.1 mols). The solution is stirred at −78° C. and the LDA (1.4 M in THF/heptane/ethylbezene, 0.15 mols, 1.5 eq.). is added dropwise via additional funnel over a period of 25 min. After addition is completed, the solution is stirred at −78° C. for additional 2 hours. The reaction mixture is quenched with water (50 mL) and diluted with t-butyl methyl ether (100 mL). The organic phase is washed with HCl (0.5 M, 100 mL), then with water (100 mL), saturated aqueous solution of NaHCO$_3$ (100 mL) and finally with brine (100 mL). The organic phase is dried over anhydrous MgSO$_4$, filtered and concentrated. Purification of dichlorocarbinol is generally not needed.

General Procedure for Tosylation of Dichlorocarbinols

In a dried, 500 mL, round-bottomed flask equipped with a magnetic stirrer and under nitrogen is dissolved the dichlorocarbinol (0.1 mols) and triethylamine (0.15 mols, 1.5 eq) in methylenechloride (200 mL) at room temperature. To this stirred solution is added toluenesulfonylchloride (0.1 mols, 1 eq) in one portion, and stirred at room temperature for one hour. After this period of time, generally, the TLC indicates completion of the reaction (depending upon substrate). The reaction is quenched with water (50 mL). The organic phase in successively washed with HCl (5 N, 100 mL), water (100 mL). The combine aqueous phase is extracted with CH$_2$Cl$_2$ (2×100 mL). The organic phases are combined and washed with an aqueous solution of NaOH (2 N, 200 mL), water (100 mL) and finally brine (100 mL). This solution is dried over MgSO$_4$, filtered and concentrated to afford dichlorotosylate, generally as solid. Purification of the crude product can be done by recrystalization in a 4:1 mixture hexane ethylacetate.-

General Procedure for Methanesulfonylation of Dichlorocarbinols

In a dried, 500 mL, round-bottomed flask equipped with a magnetic stirrer and under nitrogen is dissolved the dichlorocarbinol (0.1 mols) and triethylamine (0.15 mols, 1.5 eq) in methylenechloride (200 mL) at 0° C. To this stirred solution is added methanesulfonylchloride (0.1 mols, 1 eq) in one portion, and allow to warm up to room temperature for one hour. After this period of time, generally, the TLC indicates completion of the reaction (depending upon substrate). The reaction is quenched with water (50 mL). The organic phase in successively washed with HCl (5 N, 100 mL), water (100 mL). The combine aqueous phase is extracted with $CH_2Cl_2$ (2×100 mL). The organic phases are combined and washed with an aqueous solution of NaOH (2 N, 200 mL), water (100 mL) and finally brine (100 mL). This solution is dried over $MgSO_4$, filtered and concentrated to afford dichloro-tosylate, generally as solid. Purification of the crude product can be done by recrystalization in a 4:1 mixture hexane ethylacetate.

General Procedure for Preparation of Acetylene

In a dried, 500 mL, three neck round-bottomed flask equipped with a magnetic stirrer, additional funnel and a nitrogen inlet is dissolved the dichlorotosylate (10 mmols, 1 eq) in dried THF (100 mL). To this stirred solution at −30° C. is added MeLi (1.4 M in ether, 35 mmols, 3.5 eq) dropwise via additional funnel. After addition is completed, the reaction mixture is allowed to slowly warm to 0° C. in a period of one hour. A simple way to monitor the reaction progress is by despairing of the tosylate on TLC (hexane/ ethyl acetate, 4:1). The reaction is quenched with saturated aqueous solution of ammoniumchloride (50 mL) and diluted with t-butyl methyl ether (100 mL). The aqueous phase is separated and extracted with t-butyl methyl ether (3×50 mL). The combine organic phase is washed with brine (100 mL) and dried over $MgSO_4$ anhydrous. After filtration and condensation crude acetylene is obtained in excellent yield. For low boiling point acetylene a simple distillation is recommended from the crude mixture. Characterization of acetylene was done by spectroscopy comparison with commercially available authentic sample.

EXAMPLE 11

Preparation of Cyclopropylacetylene

Step 1: 1,1-dichloro-2-cyclopropylethanol

This preparation is a typical example for this procedure: To a stirred solution of cyclocarboxaldehyde (30 mL, 0.392 mols) and methylenechloride (63.29 mL, 1.188 mols) in THF (660 mL) at −78° C., was added LDA (2 M in THF/heptane/ethylbenzene, 0.588 mols) dropwise over a period of 20 min. The reaction mixture was stirred for additional 2 hours at −78° C. After this period of time, $^1$H-NMR of a worked up sample, indicated total despairing of aldehyde proton signal. The reaction was quenched with water (150 mL) and diluted with t-butyl methyl ether (300 mL). The organic phase was washed with HCl (0.5 M, 300 mL), water (300 mL), saturated aqueous solution of $NaHCO_3$ (300 mL) and finally with brine (300 mL). The organic phase is dried over anhydrous $MgSO_4$, filtered and concentrated by rotary evaporation. the crude 1,1-dichloro-2-cyclopropylethanol was obtained as an orange oil, 55.20 g (90%) and no further purification was required for next step. Purification could be done by distillation, b.p. :37°–43° C./2 torrs or silica-gel chromatography, hexane/ethylacetate, (5:1), TLC ($R_f$=0.48). $^1$H-NMR $\delta$($CDCl_3$): 0.52 (m, 2H), 0.65 (m, 2H), 1.08–1.20 (m, 1H), 3.33 (dd, 1H), 5.80 (d, J=5.2 Hz, 1H). $^{13}$C-NMR $\delta$($CDCl_3$): 4.05, 5.32, 12.2, 72.02, 87.95 ppm. MS($CI/NH_3$): (M+1): 156.

Step 2: 1,1-dichloro-2-cyclopropyl-2-ethyltosylate

This preparation is a typical example for this procedure: To a stirred solution of 1,1-dichloro-2-cyclopropylethanol (0.134 mols, leq) and triethylamine (0.201 mols, 1.5 eq) in methylenechloride (250 mL) at room temperature, was added toluenesulfonylchloride (0.134 mols, 1 eq) in one portion. The solution was stirred for 1.5 hours at room temperature where TLC (hexane/ethylacetate 4:1 v/v) shows no starting material left. The reaction is quenched with water (60 mL). The organic phase in successively washed with HCl (5 M, 120 mL), water (120 mL). The combine aqueous phase is extracted with $CH_2Cl_2$ (2×120 mL). The organic phases are combined and washed with an aqueous solution of NaOH (2 M, 240 mL), water (120 mL) and finally brine (120 mL). This solution is dried over $MgSO_4$, filtered and concentrated to afford 39.38 g of crude 1,1-dichloro-2-cyclopropyl-2-ethyltosylate as solid. Purification of the crude product by recrystalization using a 4:1 mixture hexane/ethylacetate afford 33 g (80%). m.p.: 92°–93° C. $^1$H-NMR $\delta$($CDCl_3$): 0.36 (m, 1H), 0.55–0.62 (m, 2H), 0.71–0.82 (m, 1H), 1.33 (m, 1H), 2.43 (s, 3H), 4.15 (dd, $J_1$=7.8 Hz, $J_2$=7.8 Hz, 1H), 5.85 (d, J=6.8 Hz, 1H), 7.37 (d, J=10.9 Hz, 2H), 7.82 (d, J=10.9 Hz, 2H). $^{13}$C-NMR $\delta$($CDCl_3$): 4.05, 5.32, 11.2, 40.35, 72.02, 87.95, 127.8 (2C), 129.9 (2C), 134.3, 144.6 ppm. MS($CI/NH_3$): (M+1): 310. $C_{12}H_{14}Cl_2O_3S$: theo.: C: 46.61%, H: 4.56%, S: 10.37%. found: C: 46.63%, H: 4.54%, S: 10.32%.

Alternative Step 2: 1,1-dichloro-2-cyclopropyl-2-ethylmethanesulfonylate

This preparation is a typical example for this procedure: To a stirred solution of 1,1-dichloro-2-cyclopropylethanol (10.0 g, 64.52 mmols, 1 eq) and pyridine (7.83 mL, 96.78 mmols, 1.5 eq) in methylenechloride (100 mL) at 0° C., was added methanesulfonylchloride (6.00 mL,, 77.42 mmols, 1.1 eq) in one portion. The solution was stirred for 1.5 hours at room temperature where TLC (hexane/ethylacetate 5:1 v/v) shown no starting material left. The reaction is quenched with water (60 mL). The organic phase in successively washed with HCl (5 M, 120 mL), water (120 mL). The combine aqueous phase is extracted with $CH_2Cl_2$ (2×120 mL). The organic phases are combined and washed with an aqueous solution of NaOH (2 M, 240 mL), water (120 mL) and finally brine (120 mL). This solution is dried over $MgSO_4$, filtered and concentrated to afford 11.92 g (80%) of crude 1,1-dichloro-2-cyclopropyl-2-ethylmethanesulfonylate as a solid. Purification by recrystalization using a 4:1 mixture hexane/ethylacetate. m.p.: 87°–88° C. $^1$H-NMR $\delta$($CDCl_3$): 0.55 (m, 2H), 0.72 (m, 2H), 1.38 (m, 1H), 1.33 (m, 1H), 3.15 (s, 3H), 4.20 (dd, $J_1$=7.8 Hz, $J_2$ =7.8 Hz, 1H), 5.90 (d, J=6.8 Hz, 1H). $^{13}$C-NMR $\delta$($CDCl_3$): 4.05, 5.32, 11.2, 39.55, 72.02, 87.95 ppm. MS(CI/NH3): (M+1): 234. $C_6H_{10}Cl_2O_3S$: theo.: C: 30.91%, H: 4.32%, S: 13.76%.

Step 3: Cyclopropylacetylene (CPA)

This preparation is a typical example for this procedure: To a stirred solution of 1,1-dichloro-2-cyclopropyl-1-ethyltosylate (29.10 mmol) in dried THF (290 mL) at −30° C. was added MeLi (1.4 M in ether, 101.9 mmol) dropwise via additional funnel. After the addition was completed, the solution was allowed to slowly warm to 0° C. in one hour period. At this time, TLC (hexane/ethyl acetate, 4:1) indicated no starting material left. The reaction was quenched with saturated aqueous solution of ammoniumchloride (120 mL) and diluted with ethyl acetate (250 mL). The aqueous phase is extracted with ethyl acetate (3×100 mL). The combine organic phase is washed with brine (150 ml.) and dried over $MgSO_4$ anhydrous. After filtration a 94% solution yield of CPA in THF/ethyl acetate is obtained. Neat CPA can be distilled by using vacuum at room temperature and condensing it in a $CO_2$/acetone trap, which afford 1.78 g (89%) of neat CPA.

Alternative Step 3

To a four necked round bottom flask equipped with a magnetic stirrer, a nitrogen outlet, and an efficient outlet connected to a bubbler, $NaNH_2$ (15.2 g, 388.4 mmol, 4 eq.) was suspended in 150 ml of DMSO (caution: severe $NH_3$ gas releasing was observed) and warmed to 40° C. under vigorous stirring to form a homogeneous solution. The solution was then cooled to 5° C. To the solution, cyclopropyl dichlorocarbinol tosylate (30 g, 97.1 mmol, 1 eq.) dissolved in 50 ml of DMSO was added slowly via addition funnel (in such a rate that internal temperature was not exceeding 20° C.) in 40 minutes. The reaction was stirred at 15° C. to 20° C. for 15 minutes after the addition. The reaction mixture was then cooled to 5° C. To the solution, water (7.9 g, 437 mmol, 4.5 eq) was added slowly (in such a rate that internal temperature was not exceeding 20° C.) in 5 minutes. After the addition, the reaction mixture was stirred at room temperature for 5 minutes. The neat CPA (5.1 g, 79.5% yield) was obtained by direct distillation under reduced pressure

EXAMPLE 12
Preparation of 3,3-dimethyl-1-butyne

The title compound was prepared according to Scheme 2 using the procedures of Example 10 and/or 11 starting from trimethylacetaldehyde. The product, 4ee, was compared to an authentic reference, the yield is listed in Example 18.

Compound 2ee; 1,1-dichloro-3,3-dimethyl-2-butanol: Yield: 87%. $^1$H-NMR $\delta$($CDCl_3$): 1.02 (s, 9H), 3.65 (d, 1H), 6.03 (d, 1H). $_{13}$H-NMR $\delta$($CDCl_3$): 28.22 (tert-butyl, 3C), 37.82, 87.88 ppm. MS(CI/$NH_3$) (M+1): 172

Compound 3ee; 1,1-dichloro-3,3-dimethyl-2-butylmethanesulfonylate: Yield: 68% m.p.: 70–71° C. $^1$H-NMR $\delta$($CDCl_3$): 1.17 (s, 9H), 3.32 (s, 3H), 5.07 (d, 1H), 6.10 (d, 1H). $^{13}$C-NMR $\delta$($CDCl_3$): 28.22 (tert-butyl, 3C), 87.88, 94.0 ppm. MS(CI/$NH_3$) (M+1): 250. $C_7H_{13}Cl_3O_3S$: theo.: C:33.73%, H: 5.66%, S: 12.87%.

EXAMPLE 13
Preparation of Cyclohexylacetylene

The title compound was prepared according to Scheme 2 using the procedures of Example 10 and/or 11 starting from cyclohexanecarboxaldehyde. The product, 4bb, was compared to an authentic reference, the yield is listed in Example 18.

Compound 2bb; 1,1-dichloro-2-cyclohexylethanol: Yield: 90%. $^1$H-NMR $\delta$($CDCl_3$): 1.05–1.40 (m, 5H), 1.65–1.80 (m, 5H), 1.95 (m, 1H) 3.91 (dd, $J_1$=8.7 Hz, $J_2$=8.8 Hz, 1H), 5.85 (d, J=7.2 Hz). $^{13}$C-NMR $\delta$($CDCl_3$): 21.80, 25.70, 25.87, 26.02, 28.00, 29.85, 39.85, 88.80 ppm. MS(CI/$NH_3$) (M+1): 198

Compound 3bb; 1,1-dichloro-2-cyclohexylethyltosylate: Yield: 93%. m.p. : 68°–69° C. $^1$H-NMR $\delta$($CDCl_3$): 1.05–1.37 (m, 5H), 1.55–1.87 (m, 5H), 1.93–2.04 (m, 1H), 2.43 (s, 3H), 4.62 (dd, $J_1$=7.3 Hz, $J_2$=7.3 Hz 1H), 5.83 (d, J=8.9 Hz, 1H) 7.35 (d, J=11.0 Hz, 2H), 7,82 (d, J=11.0 Hz, 2H). $^{13}$C-NMR $\delta$($CDCl_3$): 21.80, 25.70, 25.87, 26.02, 28.00, 29.87, 39.82, 70.03, 88.0, 127.8, 129.8, 132.0, 145.2 ppm. MS(CI/$NH_3$) (M+1): 352. $C_{15}H_{20}Cl_2O_3S$: theo.: C: 51.29%, H: 5.74%, S: 9.13%; found: C: 51.30%, H: 5.75%, S: 9.11%.

EXAMPLE 14
Preparation of Phenylacetylene

The title compound was prepared according to Scheme 2 using the procedures of Example 10 and/or 11 starting from benzaldehyde. The product, 4ff, was compared to an authentic reference, the yield is listed in Example 18.

Compound 2ff; 1,1-dichloro-2-phenylethanol: Yield: 95%. $^1$H-NMR $\delta$($CDCl_3$): 4.94 (d, J=10.1 Hz, 1H), 5.80 (d, =8.9 Hz, 1H). $^{13}$C-NMR $\delta$($CDCl_3$): 21.90, 84.02, 127.8, 127.9, 128.0, 128.2, 128.5, 129.6, 132.7 ppm. MS(CI/$NH_3$) (M+1): 192

Compounds 3ff; 1,1-dichloro-2-phenylethyltosylate: Yield: 89%. m.p.: 85°–86° C. $^1$H-NMR $\delta$($CDCl_3$): 2.37 (s, 3H), 5.63 (d, J=8.3 Hz, 1H), 5.84 (d, J=8.7 Hz, 1H), 7.14 (d, J=10.4 Hz, , 2H), 7.22–7.30 (m, 5H), 7.63 (d, J=10.4, Hz, 2H). $^{13}$C-NMR $\delta$($CDCl_3$): 21.90, 71.72, 84.03, 127.7, 127.8, 128,0 129.7, 132.5, 133.2, 145.6 ppm. MS(CI/$NH_3$) (M+1): 346. $C_{15}H_{14}Cl_2O_3S$: theo. : C: 52.18%, H: 4.07%, S: 9.29%. found: C: 52.15%, H: 4.09%, S: 9.30%.

EXAMPLE 15
Preparation of 4-methyl-1-pentyne

The title compound was prepared according to Scheme 2 using the procedures of Example 10 and/or 11 starting from isovaleraldehyde. The product, 4cc, was compared to an authentic reference, the yield is listed in Example 18.

Compound 2cc: 1,1-dichloro-3-methyl-2-pentanol: Yield: 90%. $^1$H-NMR $\delta$($CDCl_3$): 0.88 (d, J=9.8 Hz, 3H), 0.97 (d, J=9.8 Hz, 3H), 1.54 (m, 1H), 1.95 (m, 2H), 5.64 (d, J=8.3 Hz, 1H). $^{13}$C-NMR $\delta$($CDCl_3$): 21.00, 21.80, 23.1, 23.7, 35.90, 80.67 ppm. MS(CI/$NH_3$) (M+1): 173

Compound 3cc; 1,1-dichloro-3-methyl-2-pentyltosylate: Yield: 79%. m.p.: 62°–63° C. $^1$H-NMR $\delta$($CDCl_3$): 0.74 (d, J=10.0 Hz, 3H), 0.91 (d, J=10.0 Hz, 3H), 1.45–1.65 (m, 2H), 1.80–1.87 (m, 1H) 2.45 (s, 3H), 4.77 (dd, 1H), 6.0 (d, J=6.8 Hz, 1H) 7.35 (d, J=10.1 Hz, 2H), 7.82 (d, J=10.1 Hz, 2H). $^{13}$C-NMR $\delta$($CDCl_3$): 21.00, 21.80, 23.05, 23.70, 36.15, 71, 71.03, 80.92, 127.8, 129.7, 133.2, 145.7 ppm. MS(CI/$NH_3$) (M+1): 322. $C_{13}H_{18}Cl_2O_3S$: theo.: C: 48.00%, H: 5.58%, S: 9.85%. found: C: 48.03%, H: 5.58%, S: 9.84%.

EXAMPLE 16
Preparation of 4-phenyl-1-butyne

The title compound was prepared according to Scheme 2 using the procedures of Example 10 and/or 11 starting from 3-phenylpropionaldehyde. The product, 4gg, was compared to an authentic reference, the yield is listed in Example 18.

Compound 2gga; 1,1-dichloro-4-phenyl-2-butanol: Yield: 89%. $^1$H-NMR $\delta$($CDCl_3$): 2.18–2.30 (m, 2H), 2.40–2.53 (m, 1H), 7.23–2.95 (m, 3H), 4.38 (dd, 1H), 7.17–7.25 (m, 3H). $^{13}$C-NMR $\delta$($CDCl_3$): 21.90, 31.80, 33.95, 99.2, 127.3, 127.9, 128.4, 128.9 ppm. MS(CI/NH3) (M+1): 220

Compound 3ggq; 1,1-dichloro-4-phenyl-2-butyltosylate: Yield: 82%. m.p.: 58°–59° C. $^1$H-NMR $\delta$($CDCl_3$): 2.18–2.30 (m, 2H), 2.31–2.44 (m, 1H) 2.42 (s, 3H), 2.60–2.70 (m, 1H), 4.71 (dd, 1H), 7.17 (d, J=10.0 Hz, 2H), 7.12–7.30 (m, 3H), 7.34 (d, J=9.8 Hz, 2H), 7.82 (d, J=10.0 Hz, 2H). $^{13}$C-NMR $\delta$($CDCl_3$) 21.90, 29.87, 30.90, 71.72, 82.00, 126.9, 128.0, 128.2, 128.4, 129.8, 133.6, 139.8, 145.5 ppm. MS(CI/$NH_3$) (M+1): 374. $C_{17}H_{18}Cl_2O_3S$: theo. : C: 54.76%, H: 4.86%, S: 8.60%. found.: C: 54.78%, H: 4.84%, S: 8.58%.

EXAMPLE 17
Preparation of 1-Decyne

The title compound was prepared according to Scheme 2 using the procedures of Example 10 and/or 11 starting from nonyl aldehyde. The product, 4dd, was compared to an authentic reference, the yield is listed in Example 18.

Compound 2dd: 1,1-dichloro-2-decanol: Yield: 82%. $^1$H-NMR $\delta$($CDCl_3$): 0.88 (t, 3H), 1.20–1.53 (m, 10H), 1.80–1.90 (m, 2H), 4.15 (m, 1H), 5.22 (d, J=7.2, 1H).

$^{13}$C-NMR δ(CDCl$_3$): 14.00, 21.90, 22.12, 25.52, 29.87, 29.92, 31.82, 31.90, 89.20 ppm. MS(CI/NH$_3$) (M+1): 228
Compound 3dd; 1,1-dichloro-2-decanyltosylate: Yield: 74%. oil. Silica-gel chromatography (hexane/ethylacetate 4:1). $^1$H-NMR δ(CDCl$_3$): 0.88 (t, 3H), 1.19–1.55 (m, 10H), 1.80–1.91 (m, 2H), 2.42 (s, 3H), 4.48 (m, 1H), 5.87 (d, J=6.4 Hz, 1H), 7.35 (d, J=9.8 Hz, 2H), 7.80 (d, J=9.8 Hz, 2H).

$^{13}$C-NMR δ(CDCl$_3$): 14.00, 21.90, 22.12, 24.22, 28.03, 29.44, 29.48, 29.57, 29.60, 31.92, 72.00, 80.97, 128.4, 129.8, 129.8, 133.0, 145.3 ppm. MS(CI/NH$_3$) (M+1): 382. C$_{17}$H$_{26}$Cl2O$_3$S: theo.: C: 53.54%, H: 6.87%, S: 8.41%.

EXAMPLE 18

TABLE 2

Compounds prepared by the procedures of Scheme 3.

| Formula | 2 | Yield (%)[a] | 3 | Yield (%)[b] | 4 | Yield (%)[c] |
|---|---|---|---|---|---|---|
| aa | cyclopropyl-CH(OH)-CHCl$_2$ | 83 | cyclopropyl-CH(OTs)-CHCl$_2$ | 80 | cyclopropyl-C≡CH | 89[d] |
| bb | cyclohexyl-CH(OH)-CHCl$_2$ | 90 | cyclohexyl-CH(OTs)-CHCl$_2$ | 93 | cyclohexyl-C≡CH | 91 |
| cc | isobutyl-CH(OH)-CHCl$_2$ | 90 | isobutyl-CH(OTs)-CHCl$_2$ | 79 | isobutyl-C≡CH | 92[d] |
| dd | CH$_3$(CH$_2$)$_7$-CH(OH)-CHCl$_2$ | 82 | CH$_3$(CH$_2$)$_7$-CH(OTs)-CHCl$_2$ | 74 | CH$_3$(CH$_2$)$_7$-C≡CH | 93 |
| ee | t-Bu-CH(OH)-CHCl$_2$ | 87 | t-Bu-CH(OMs)-CHCl$_2$ | 68 | t-Bu-C≡CH | 78[d] |
| ff | Ph-CH(OH)-CHCl$_2$ | 95 | Ph-CH(OTs)-CHCl$_2$ | 84 | Ph-C≡CH | 93 |
| gg | Ph-CH$_2$CH$_2$-CH(OH)-CHCl$_2$ | 89 | Ph-CH$_2$CH$_2$-CH(OTs)-CHCl$_2$ | 82 | Ph-CH$_2$CH$_2$-C≡CH | 97 |

[a]No purification is needed for next step.
[b]Base on recrystalized product; hexane/ethyl acetate (4:1).
[c]Base on isolated yield, otherwise indicated.
[d]Solution yield by GC.

What is claimed is:

1. A process for synthesis of a compound of formula (IV);

(IV)

wherein:

$R^1$ is selected from:
  $C_{1-10}$ alkyl substituted with 0–3 $R^4$,
  $C_{2-6}$ alkenyl substituted with 0–1 $R^4$,
  $C_{3-10}$ cycloalkyl substituted with 0–2 $R^5$,
  $C_{3-6}$ carbocyclic ring substituted with 0–2 $R^5$, and
  aryl substituted with 0–2 $R^6$;

$R^4$, at each occurrence, is selected from $OR^7$, $NR^7R^{7a}$, phenyl, and cyclopropyl;

$R^5$, at each occurrence, is selected from D, methyl, ethyl, propyl, methoxy, ethoxy, and propoxy;

$R^6$, at each occurrence, is selected from methyl, ethyl, propyl, methoxy, ethoxy, propoxy, F, Cl, B, I, CN, and $NR^7R^{7a}$;

$R^7$ and $R^{7a}$ are independently selected from methyl, ethyl, propyl, and butyl;

said process comprising:

(1) contacting an aldehyde of formula $R^1$—CHO with trichloroacetic acid or tribromoacetic acid, in the presence of a base catalyst to form a compound of formula (II):

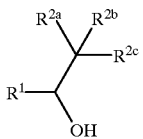
(II)

wherein $R^{2a}$, $R^{2b}$, and $R^{2c}$ are Cl or Br;

(2) contacting a compound of formula (II) with a hydroxy group protecting agent in the presence of a coupling catalyst and an acid scavenger, in a suitable nonaqueous solvent to form a compound of formula (III)

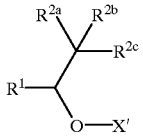
(III)

wherein —X' is a hydroxy protecting group; and (3) contacting a compound of formula (III) with a strong base to form a compound of formula (IV).

2. A process of claim 1 for synthesis of cyclopropylacetylene, said process comprising:

(1) contacting cyclopropane carboxaldehyde with trichloroacetic acid or tribromoacetic acid, in the presence of a base catalyst to form a compound of formula (IIa)

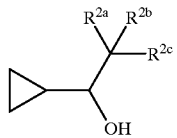
(IIa)

wherein $R^{2a}$, $R^{2b}$, and $R^{2c}$ are Cl or Br;

(2) contacting a compound of formula (IIa) with a sulfonyl hydroxy group protecting agent in the presence of a coupling catalyst and an acid scavenger, in a suitable nonaqueous solvent to form a compound of formula (IIIa)

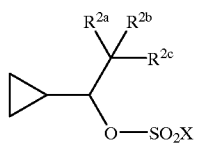
(IIIa)

wherein —$SO_2X$ is a sulfonyl hydroxy protecting group; and (3) contacting a compound of formula (IIIa) with a strong base to form cyclopropyl acetylene.

3. The process of claim 2 wherein cyclopropane carboxaldehyde is contacted with trichloroacetic acid in the presence of a base catalyst to form a compound of formula (IIa) wherein $R^{2a}$, $R^{2b}$, and $R^{2c}$ are Cl.

4. The process of claim 2 wherein the sulfonyl hydroxy group protecting agent comprises toluenesulfonyl chloride or methanesulfonyl chloride.

5. The process of claim 2 wherein the base catalyst comprises sodium trichloroacetate.

6. The process of claim 2 wherein the coupling catalyst comprises 1,4-diazabicyclo[2.2.2]octane.

7. The process of claim 2 wherein the acid scavenger comprises triethylamine.

8. The process of claim 2 wherein the strong base comprises sodium amide or methyl lithium.

9. The process of claim 2 wherein the base catalyst is sodium trichloroacetate; the coupling catalyst is 1,4-diazabicyclo[2.2.2]octane; the acid scavenger is triethylamine; and the strong base is sodium amide or methyl lithium.

10. The process of claim 9 wherein the synthesis of cyclopropylacetylene comprises:

(1) contacting cyclopropane carboxaldehyde with trichloroacetic acid in the presence of trichloroacetic acid to form a compound of formula (IIa)

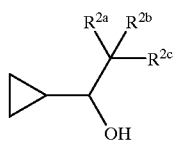
(IIa)

wherein $R^{2a}$, $R^{2b}$, and $R^{2c}$ is Cl;-

(2) contacting a compound of formula (IIa) with a toluenesulfonyl chloride or methanesulfonyl chloride in the presence of 1,4-diazabicyclo[2.2.2]octane and triethylamine, in a suitable nonaqueous solvent to form a compound of formula (IIIa)

(IIIa)

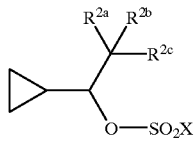

wherein —$SO_2X$ is toluenesulfonyl or methanesulfonyl; and (3) contacting a compound of formula (IIIa) with a methyl lithium or sodium amide to form cyclopropyl acetylene.

11. A process for synthesis of a compound of formula (IV);

(IV)

wherein:

$R^1$ is selected from:

$C_{1-10}$ alkyl substituted with 0–3 $R^4$, $C_{2-6}$ alkenyl substituted with 0–1 $R^4$, $C_{3-10}$ cycloalkyl substituted with 0–2 $R^5$, $C_{3-6}$ carbocyclic ring substituted with 0–2 $R^5$, and aryl substituted with 0–2 $R^6$;

$R^4$, at each occurrence, is selected from $OR^7$, $NR^7R^{7a}$, phenyl, and cyclopropyl;

$R^5$, at each occurrence, is selected from D, methyl, ethyl, propyl, methoxy, ethoxy, and propoxy;

$R^6$, at each occurrence, is selected from methyl, ethyl, propyl, methoxy, ethoxy, propoxy, F, Cl, B, I, CN, and $NR^7R^{7a}$;

$R^7$ and $R^{7a}$ are independently selected from methyl, ethyl, propyl, and butyl;

said process comprising:

(1) contacting an aldehyde of formula $R^1$—CHO with dichloromethane or dibromomethane, in the presence of a base catalyst to form a compound of formula (II):

(II)

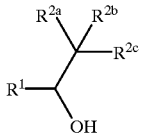

wherein: $R^{2a}$ is H and $R^{2b}$ and $R^{2c}$ are Cl or Br;

(2) contacting a compound of formula (II) with a hydroxy group protecting agent in the presence of an acid scavenger, in a suitable nonaqueous solvent to form a compound of formula (III)

(III)

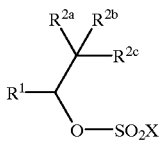

wherein —$SO_2X$ is a hydroxy protecting group; and (3) contacting a compound of formula (III) with a strong base to form a compound of formula (IV).

12. A process of claim 11 for synthesis of cyclopropylacetylene, said process comprising:

(1) contacting cyclopropane carboxaldehyde with dichloromethane or dibromomethane, in the presence of a base catalyst to form a compound of formula (IIaa)

(IIaa)

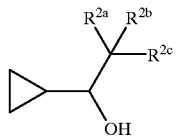

wherein: $R^{2a}$ is H and $R^{2b}$ and $R^{2c}$ are Cl or Br;

(2) contacting a compound of formula (IIaa) with a sulfonyl hydroxy group protecting agent in the presence of a coupling catalyst and an acid scavenger, in a suitable nonaqueous solvent to form a compound of formula (IIIaa)

(IIIaa)

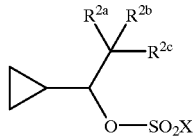

wherein —$SO_2X$ is a sulfonyl hydroxy protecting group; and (3) contacting a compound of formula (IIIaa) with a strong base to form cyclopropyl acetylene.

13. The process of claim 12 wherein cyclopropane carboxaldehyde is contacted with dichloromethane in the presence of a base catalyst to form a compound of formula (IIaa) wherein $R^{2a}$ is H and $R^{2b}$ and $R^{2c}$ are Cl.

14. The process of claim 12 wherein the sulfonyl hydroxy group protecting agent comprises toluenesulfonyl chloride or methanesulfonyl chloride.

15. The process of claim 12 wherein the base catalyst comprises sodium trichloroacetate.

16. The process of claim 12 wherein the acid scavenger comprises triethylamine.

17. The process of claim 12 wherein the strong base comprises sodium amide or methyl lithium.

18. The process of claim 12 wherein the base catalyst is sodium trichloroacetate; the acid scavenger is triethylamine; and the strong base is sodium amide or methyl lithium.

19. The process of claim 18 wherein the sulfonyl hydroxy group protecting agent comprises toluenesulfonyl chloride or methanesulfonyl chloride.

* * * * *